(12) United States Patent
Ying et al.

(10) Patent No.: US 6,767,859 B2
(45) Date of Patent: Jul. 27, 2004

(54) NON-ZEOLITIC NANOCOMPOSITE MATERIALS OF SOLID ACID CATALYSIS

(75) Inventors: Jackie Y. Ying, Winchester, MA (US); Jinsuo Xu, Springfield, NJ (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/214,376

(22) Filed: Aug. 7, 2002

(65) Prior Publication Data

US 2003/0069131 A1 Apr. 10, 2003

Related U.S. Application Data

(60) Provisional application No. 60/310,712, filed on Aug. 7, 2001.

(51) Int. Cl.⁷ ............................................. B01J 23/16
(52) U.S. Cl. ...................................... 502/305; 502/313
(58) Field of Search ................................. 502/304, 305, 502/308, 309, 310, 311, 313, 314, 316, 322, 327, 332, 333, 334, 336, 338, 339, 213, 221, 223; 585/482

(56) References Cited

U.S. PATENT DOCUMENTS

| | | | | |
|---|---|---|---|---|
| 3,878,089 A | * | 4/1975 | Wilhelm ...................... 208/139 |
| 3,879,484 A | * | 4/1975 | Pollitzer .................. 260/668 A |
| 3,997,618 A | * | 12/1976 | Cornely et al. ......... 260/668 A |
| 4,152,246 A | * | 5/1979 | Weisang et al. ............. 208/139 |
| 4,197,188 A | * | 4/1980 | Antos .......................... 208/139 |
| 4,207,209 A | * | 6/1980 | Matsuda et al. ............. 252/462 |
| 4,753,916 A | * | 6/1988 | Carcia et al. ............... 502/321 |
| 4,808,563 A | * | 2/1989 | Velenyi ....................... 502/241 |
| 5,120,898 A | * | 6/1992 | Baba et al. .................. 585/750 |
| 5,128,305 A | * | 7/1992 | Yoshimoto et al. ......... 502/243 |
| 5,179,059 A | | 1/1993 | Domesle et al. ............ 502/303 |
| 5,422,327 A | * | 6/1995 | Soled et al. ................. 502/242 |
| 6,177,382 B1 | * | 1/2001 | Hesse et al. ................. 502/439 |
| 6,316,381 B1 | | 11/2001 | Auer et al. .................. 502/185 |
| 6,387,842 B1 | * | 5/2002 | Wegman et al. ............. 502/300 |

OTHER PUBLICATIONS

Barton et al; " Structural and Catalytic Characterization of Solid Acids Based on Zirconia Modified by Tungsten Oxide", Journal of Catalysis 181: 57–72, (1999).

Hua et al; " Promoting Effect of Al on SO24– $IM_x O_y$ (M=Zr, Ti, Fe) Catalysts", Journal of Catalysis 196:104–114 (2000).

Kuba et al.; " An Active and Selective Alkane Isomerization Catalyst: Iron–and Platinum–Promoted Tungstated Zirconia", Chem. Comm. Pp.321–322, (2001).

Santiesteban et al.; " H–Spillover and SMSI Effects in Paraffin Hydroisomerization Over PT/WO X/ ZrO2 Bifunctional Catalysts", Journal of Catalysis 183: 314–322, (1999).

Scheithauer et al.; "n–Pentane Isomerization Catalysed by Fe–and Mn–Containing Tungstated Zirconia Characterization by Raman Spectroscopy" Journal of Catalysis 191:271–274 (2000).

* cited by examiner

*Primary Examiner*—Stanley S. Silverman
*Assistant Examiner*—Edward M. Johnson
(74) *Attorney, Agent, or Firm*—Dana M. Gordon; Foley Hoag LLP

(57) ABSTRACT

One aspect of the present invention relates to a catalytic compound of anion-modified metal oxides doped with metal ions. Another aspect of the present invention relates to a method of isomerizing an alkane or alkyl moiety.

26 Claims, 19 Drawing Sheets

NON-ZEOLITIC NANOCOMPOSITE MATERIALS OF SOLID ACID CATALYSIS

RELATED APPLICATIONS

This application claims the benefit of priority to U.S. Provisional Patent Application serial No. 60/310,712, filed Aug. 7, 2001; the Specification and Drawings of which are hereby incorporated by reference.

BACKGROUND OF THE INVENTION

Heterogeneous catalysis has played a critical role in many chemical processes. The impact of heterogeneously catalyzed processes on the global economy has been estimated at 20% of the world GNP, i.e., roughly $5 trillion/year. The main industrial applications of heterogeneous catalysis are petroleum refining, chemical production, and environmental protection. Petroleum refining involves the largest volume of materials processed, with the world oil refining capacity in excess of $3.6 \times 10^{12}$ kg/year.

Acid catalysis forms the basis of the most highly utilized hydrocarbon conversion processes in the petroleum industry, and constitutes an active field of research today. Although the industrial processes, such as paraffin isomerization, alkylation, catalytic cracking, and naphtha reforming, lead to different end-products, they all depend on materials with surface acidity. Environmental problems with the upstream of the refined hydrocarbon products have goaded the search for improved acid catalysts. In the production of motor-grade fuel through alkylation of isobutane with alkenes, $H_2SO_4$ or HF is used as the catalyst. These liquid mineral acids are corrosive, dangerous to handle, and difficult to dispose of. Even some industrial solid acid catalysts are environmentally harmful. For example, the bifunctional Pt-doped chlorinated alumina catalyst used in the n-butane isomerization process requires the addition of chlorinated compounds to maintain catalytic activity because it leaches corrosive HCl during use.

More significant are the problems concerning the downstream use of the hydrocarbon products, especially the deleterious emissions from the combustion of gasoline motor fuel. Addressing this was the Clean Air Act Amendments of 1990, which mandated the reformulation of motor fuel gasoline (40–50% of all petroleum products in the US). As a result, demand for particular blend components has heightened, increasing the load on existing catalytic processes. Aluminosilicate zeolites have attempted to address these environmental issues, but there is much more room for improvement, given the development of novel solid acidic materials.

Aluminosilicate zeolites are microporous, crystalline materials composed of $AlO_4$ and $SiO_4$ tetrahedra arranged around highly ordered channels and/or cavities. Zeolites are acidic solids, in which the surface acidity is generated by protons required for charge balance of the framework and located near the Al cations. More generally referred to as molecular sieves, these materials have structural properties desirable for solid acid catalysts, such as surface acidity, high surface areas, and uniform pore sizes. Examples of zeolites used as solid acids in petroleum refining include Pt/mordenite for C5/C6 isomerization, ZSM-5 for xylene isomerization and methanol-to-gasoline conversion, sulfided NiMo/faujasite for hydrocracking of heavy petroleum fractions, and USY for fluidized catalytic cracking. Zeolites are also used for other acid-catalyzed processes. The main difficulty in employing zeolites as acid catalysts lies in their great tendency to deactivate and their limited usefulness in reactions involving large molecules. Zeolites are restricted to particular compositions, pore sizes and pore structures, which limit their applicability.

A plethora of non-zeolitic materials with surface acidic properties have been investigated as potential solid acid catalysts. Superacidity is beneficial for acid-catalyzed hydrocarbon reactions because lower operation temperatures are required. Moreover, superacidic materials exhibit strong acidity and high activity for hydrocarbon reactions that are difficult to catalyze. Particularly interesting are the so-called "superacids", which have acidic strengths greater than 100% $H_2SO_4$. Sulfated zirconia and tungstated zirconia are well-studied examples of "superacidic" solids. Tungstated alumina is another example of a strongly acidic material.

The most challenging aspect in the isomerization of mid-distillates is to obtain high selectivity for isomerization vs. cracking at high conversion. Sulfated zirconia is active in converting hydrocarbons even at temperatures below 100° C., but it favors cracking reactions. Iglesia et al. (1996) found that at 200° C. with about 50% n-heptane conversion, isomerization selectivities were 85% on $Pt/WO_3/ZrO_2$, but only 35% on $Pt/SO_4^{2-}/ZrO_2$. Currently, zeolites and tungstated zirconia are the two most studied solid acids for the isomerization of mid-distillates due to the selectivity and stability of these catalysts. The benefits of using non-zeolitic materials include greater compositional flexibility, and therefore greater control of surface acidity, higher thermal and hydrothermal stability, and lower catalyst cost.

SUMMARY OF THE INVENTION

In certain embodiments, the catalytic compounds of the invention are represented by the generalized formula:

$$R_1/R_4/R_2-R_3$$

wherein:

$R_1$ is a metal or metal alloy or bimetallic system;

$R_2$ is any metal dopant;

$R_3$ is a metallic oxide or mixtures of any metallic oxide;

$R_4$ is selected from $WO_x$, $MoO_x$, $SO_4^{2-}$ or $PO_4^{3-}$; and x is a whole or fractional number between 2 and 3 inclusive.

In a particular embodiment, $R_1$ is selected from a Group VIII noble metal or a combination of Group VIII noble metals. In another embodiment, $R_1$ is selected from platinum, palladium, iridium, rhodium, or a combination of these. In yet another embodiment, $R_1$ is a Pt—Sn, Pt—Pd, or Pt—Ga alloy or bimetallic system.

In a particular embodiment, $R_2$ is selected from the group $Al^{3+}$, $Ga^{3+}$, $Ce^{4+}$, $Sb^{5+}$, $Sc^{3+}$, $Mg^{2+}$, $Co^{2+}$, $Fe^{3+, Cr3+}$, $Y^{3+}$, $Si^{4+}$, and $In^{3+}$.

In another particular embodiment, $R_3$ is selected from the group zirconium oxide, titanium oxide, tin oxide, ferric oxide, cerium oxide or mixtures thereof. In another particular embodiment, $R_4$ is selected from $SO_4^{2-}$, $WO_x$, $MoO_x$, $PO_4^{3-}$, $W_{20}O_{58}$, $WO_{29}$ and anions and mixtures thereof. In a particular embodiment, the metallic oxide is $ZrO_2$. In a particular embodiment, x about 3.

In one embodiment, the ratio of metal dopant to metal in the oxide is less than or equal to about 0.20. In another embodiment, the ratio of metal dopant to metal in the oxide is less than or equal to about 0.05. In yet another embodiment, the ratio of metal dopant to metal in the oxide is about 0.05.

In another embodiment, the catalytic compounds of the present invention are represented by $Pt/WO_3/Al$—$ZrO_2$ Another aspect of this invention is a method of alkane and alkyl moiety isomerizations comprising the step of contacting a catalyst with an alkane or alkyl, wherein said catalyst comprises:

$$R_1/R_4/R_2-R_3$$

wherein:

$R_1$ is a metal or metal alloy or bimetallic system;

$R_2$ is any metal dopant;

$R_3$ is a metallic oxide or mixtures of any metallic oxide;

$R_4$ is selected from $WO_x$, $SO_4^{2-}$, $MoO_x$, or $PO_4^{3-}$; and x is a whole or fractional number between 2 and 3 inclusive.

In a preferred embodiment, the catalysts are used for conversion of straight chain or n-alkyls. In certain embodiments, the n-alkyl is a straight chain lower alkane, or $C_4-C_7$ alkane. In certain other embodiments, the n-alkyl is n-hexane, n-octane, or n-heptane. In a particular embodiment, the n-alkyl is n-heptane.

In one embodiment, the temperature of the reaction was lower than 210° C., lower than 170° C., lower than 150° C. In another embodiment, the isomerization conversions are higher than 80%. In yet another embodiment, the catalyst compounds are used in a process to produce alkane or alkyl moiety isomers with a yield of greater than 70%, greater than 80% of the reaction product. In a further embodiment, the catalyst compounds were used to produce alkanes in the form of higher octane number, multi-branched alkanes.

DETAILED DESCRIPTION OF THE INVENTION

A. Overview

Figure 1:
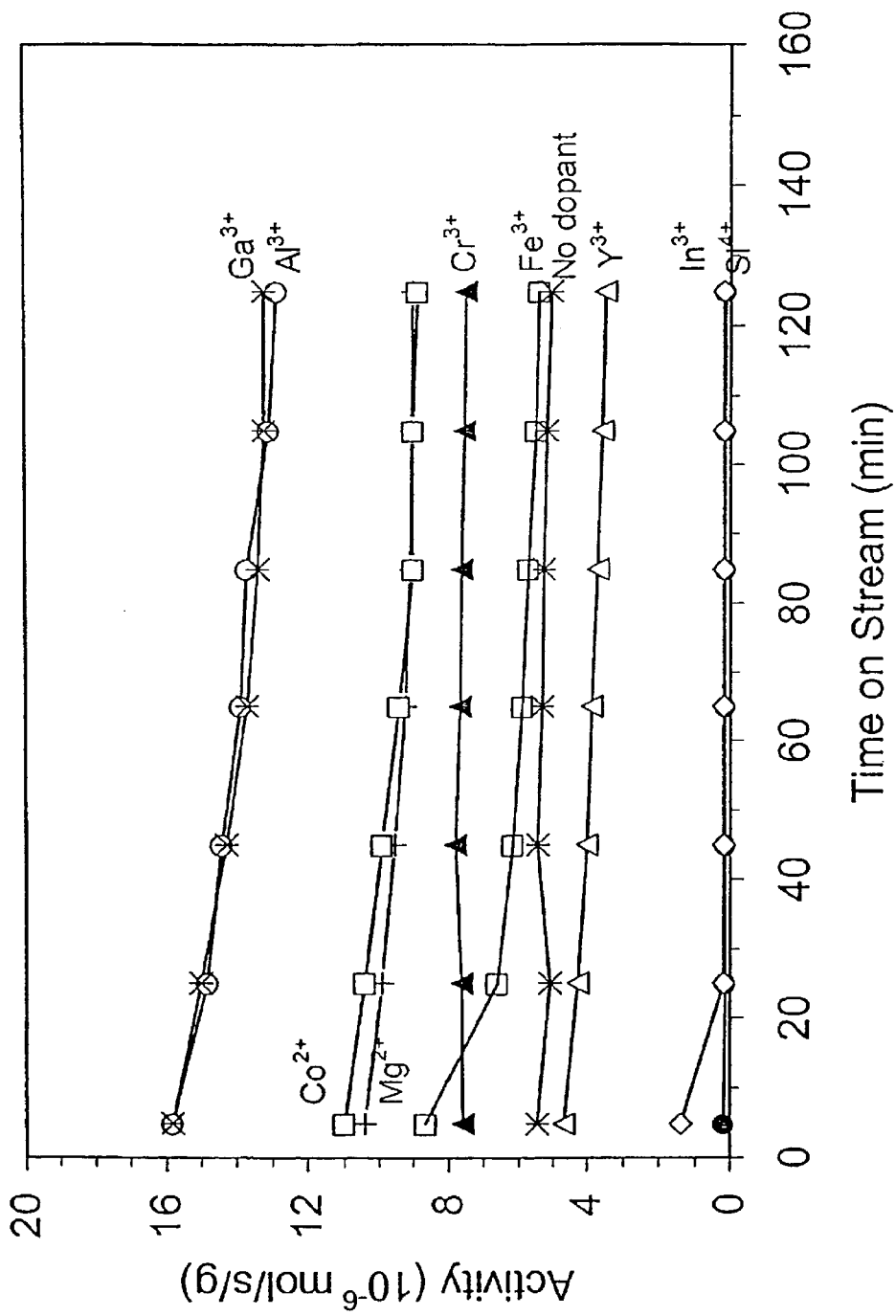
FIG. 1 depicts the activity of $Pt/WO_3/M-ZrO_2$ with different dopants (M/Zr=0.05, 800° C.) in n-heptane isomerization.

The present invention relates to a catalytic compound of anion-modified metal oxides doped with metal ions. The present invention also relates to n-alkane and alkyl moiety isomerization process comprising a catalytic compound of the present invention.

In certain embodiments, metallic dopants in a catalytic compound greatly increased the activity of tungstated metal oxides with noble metals. These noble metal/anion/metal-doped metal oxide materials catalyzed the isomerization of n-alkanes and alkyl moieties with high selectivities.

In certain aspects of the present invention the catalytic materials are used in a isomerization conversion reaction or process. Such a process has a low reaction temperature, and provides for high isomerization conversion yield.

B. Definitions

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1-C_{30}$ for straight chain, $C_3-C_{30}$ for branched chain), and more preferably 20 of fewer. Likewise, preferred cycloalkyls have from 4–10 carbon atoms in their ring structure, and more preferably have 5, 6 or 7 carbons in the ring structure.

The terms "alkenyl" and "alkynyl" refer to unsaturated aliphatic groups analogous in length and possible substitution to the alkyls described above, but which contain at least one double or triple carbon—carbon bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

C. Compounds

The compounds of the invention are catalytic compounds represented by the generalized formula:

wherein:

$R_1$ is a metal or metal alloy or bimetallic system;

$R_2$ is any metal dopant;

$R_3$ is a metallic oxide or mixtures of any metallic oxide;

$R_4$ is $WO_x$, $MoO_x$, $SO_4^{2-}$, or $PO_4^{3-}$; and x is a number between 2 and 3 inclusive.

In a particular embodiment, $R_1$ is selected from a Group VIII noble metal or a combination of Group VIII noble metals. In another embodiment, $R_1$ is selected from platinum, palladium, iridium, rhodium, or a combination of these. In yet another embodiment, $R_1$ is a Pt—Sn, Pt—Pd, or Pt—Ge alloy or bimetallic system.

In a particular embodiment, $R_2$ is selected from the group $Al^{3+}$, $Ga^{3+}$, $Ce^{4+}$, $Sb^{5+}$, $Sc^{3+}$, $Mg^{2+}$, $Co^{2+}$, $Fe^{3+}$, $Cr^{3+}$, $Y^{3+}$, $Si^{4+}$, and $In^{3+}$. In another embodiment, $R_2$ is $Al^{3+}$.

In another particular embodiment, the metallic oxide is zirconium oxide, titanium oxide, ferric oxide, cerium oxide, tin oxide, $SO_4^{2-}$, and anions and mixtures thereof. In a particular embodiment, the metallic oxide is $ZrO_2$.

In another embodiment, x is about 3.

In one embodiment, the ratio of metal dopant to metal in the oxide is less than or equal to about 0.20. In another embodiment, the ratio of metal dopant to metal in the oxide is less than or equal to about 0.05. In yet another embodiment, the ratio of metal dopant to metal in the oxide is about 0.05.

In another embodiment, the catalytic compounds of the present invention are represented by Pt/WO$_3$/Al—ZrO$_2$.

In an aspect of the present invention, the catalytic compounds are used for conversion of straight chain alkyls to branched alkyls. In a preferred embodiment, the catalysts are used for conversion of straight chain or n-alkyls. As shown in FIG. 1, doping ZrO$_2$ with different cations changed the activity of Pt/WO$_3$/ZrO$_2$ dramatically. Dopants such as Al$^{3+}$ and Ga$^{3+}$ increased the catalyst activity by 2–3 times. This promotion effect is not related to the acidity/basicity of the dopant oxide or to the reduction potential of the dopant cation. For example, MgO and Y$_2$O$_3$ are both basic oxides, but Mg$^{2+}$ dopant increased the activity. The reduction potentials of Al$^{3+}$, Cr$^{3+}$, and Co$^{2+}$ are very different from each other; however, they all increased the activity of tungstated zirconia with Pt.

Herein a shorthand notation for catalytic compounds is used. For example, Pt/AlWZ(0.05, 800° C.) is a platinum tungstated zirconia catalyst doped with Al$^{3+}$ with a ratio of Al/Zr of 0.05 and calcinated at 800° C.

Figure 2:
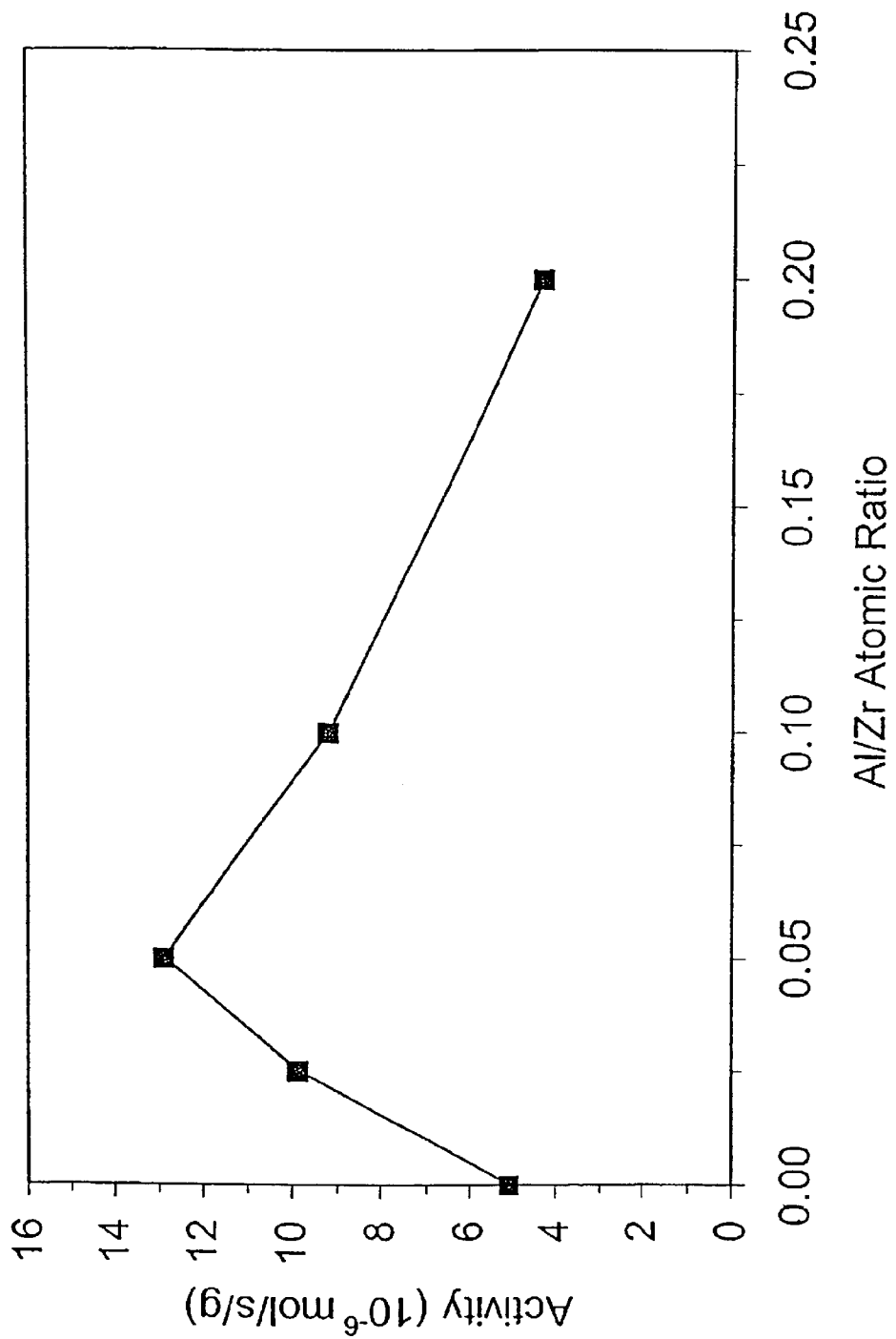
FIG. 2 depicts the effect of $Al^{3+}$ doping level on the n-heptane isomerization activity of Pt/AlWZ(800° C.).

In an embodiment, the ratio of Al to Zr is ≦0.05. Different amounts of Al$^{3+}$ ion were introduced into zirconia in the preparation of Pt/AlWZ(800° C.). FIG. 2 showed that at low doping levels (Al/Zr≦0.05), the activity of Pt/AlWZ(800° C.) increased with the amount of dopant. However, at high doping levels, the activity of Pt/AlWZ(800° C.) decreased with the amount of dopant. Doping Al$^{3+}$ and Ga$^{3+}$ ions into zirconia promoted the activity of Pt/WO$_3$/ZrO$_2$ by 2–3 times. Here, Pt/AlWZ(0.05, 800° C.) was chosen representatively to convert a series of mid-distillates, such as n-hexane, n-heptane and n-octane. The isomerization selectivities vs. total conversions of the three hydrocarbons are shown in FIG. 3 to FIG. 8.

Figure 3:
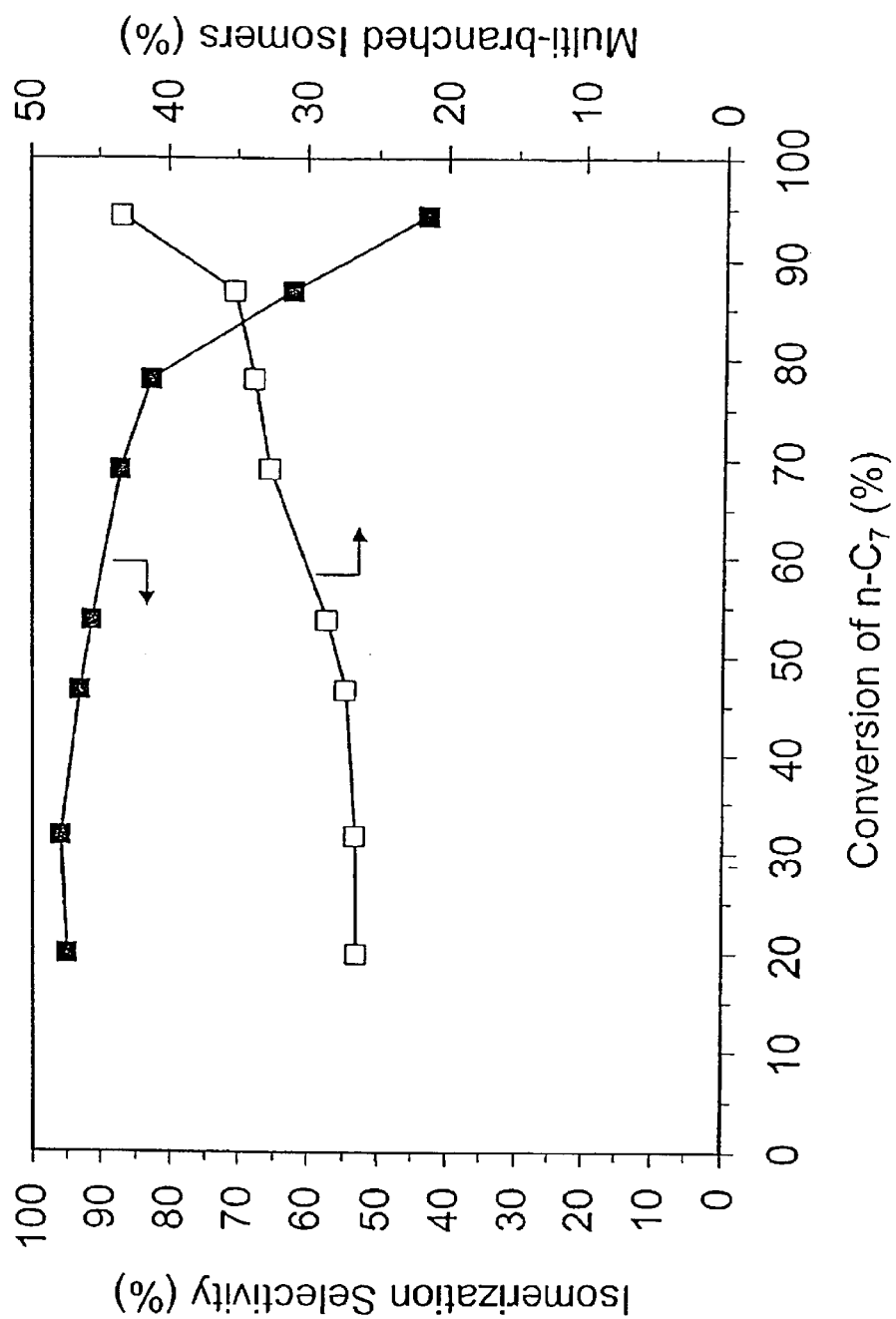
FIG. 3 depicts the n-heptane isomerization selectivity vs. conversion over Pt/AlWZ(0.05, 800° C.) at 200° C. in $H_2$.
Figure 4:
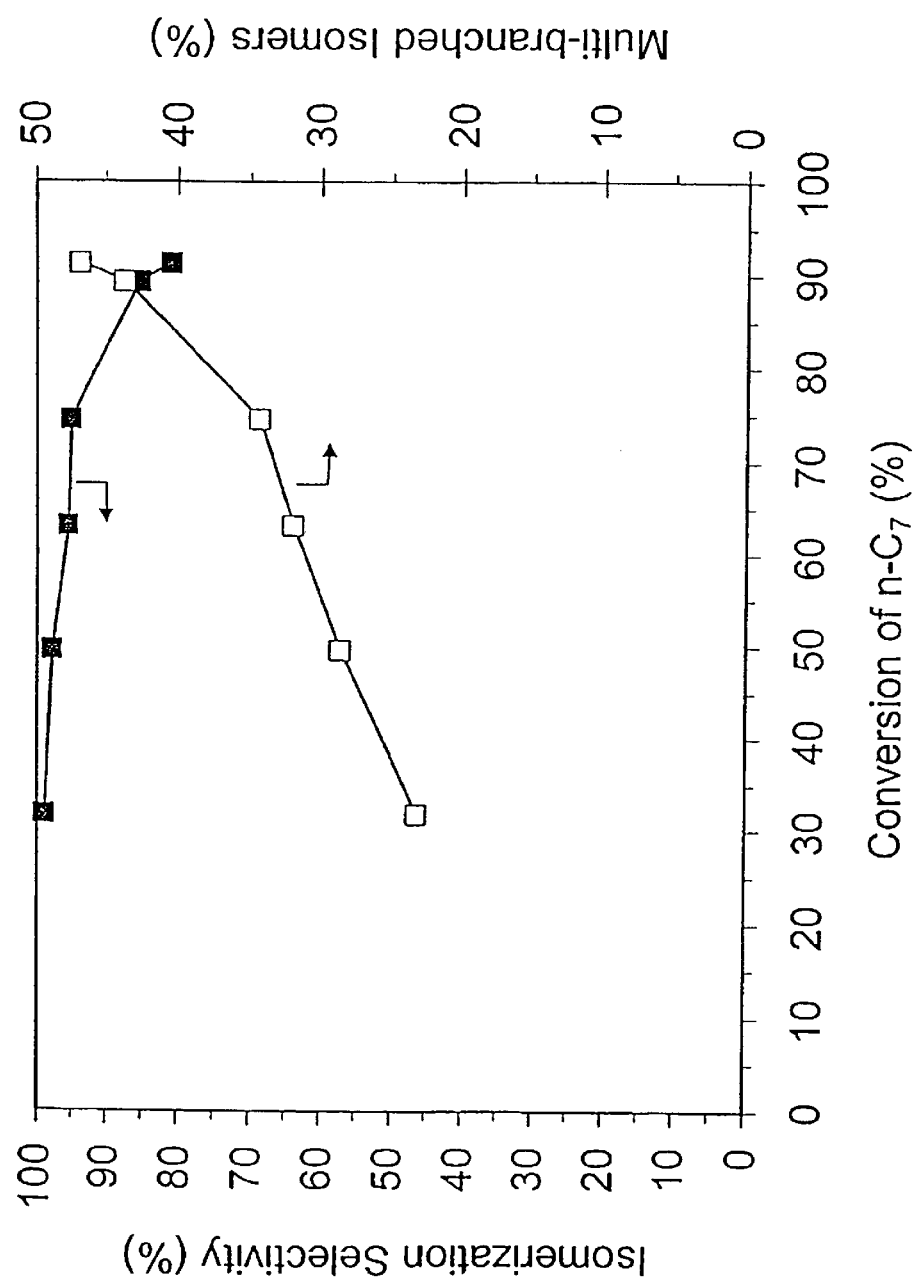
FIG. 4 depicts the n-heptane isomerization selectivity vs. conversion over Pt/AlWZ(0.05, 800° C.) at 150° C. in $H_2$.
Figure 5:
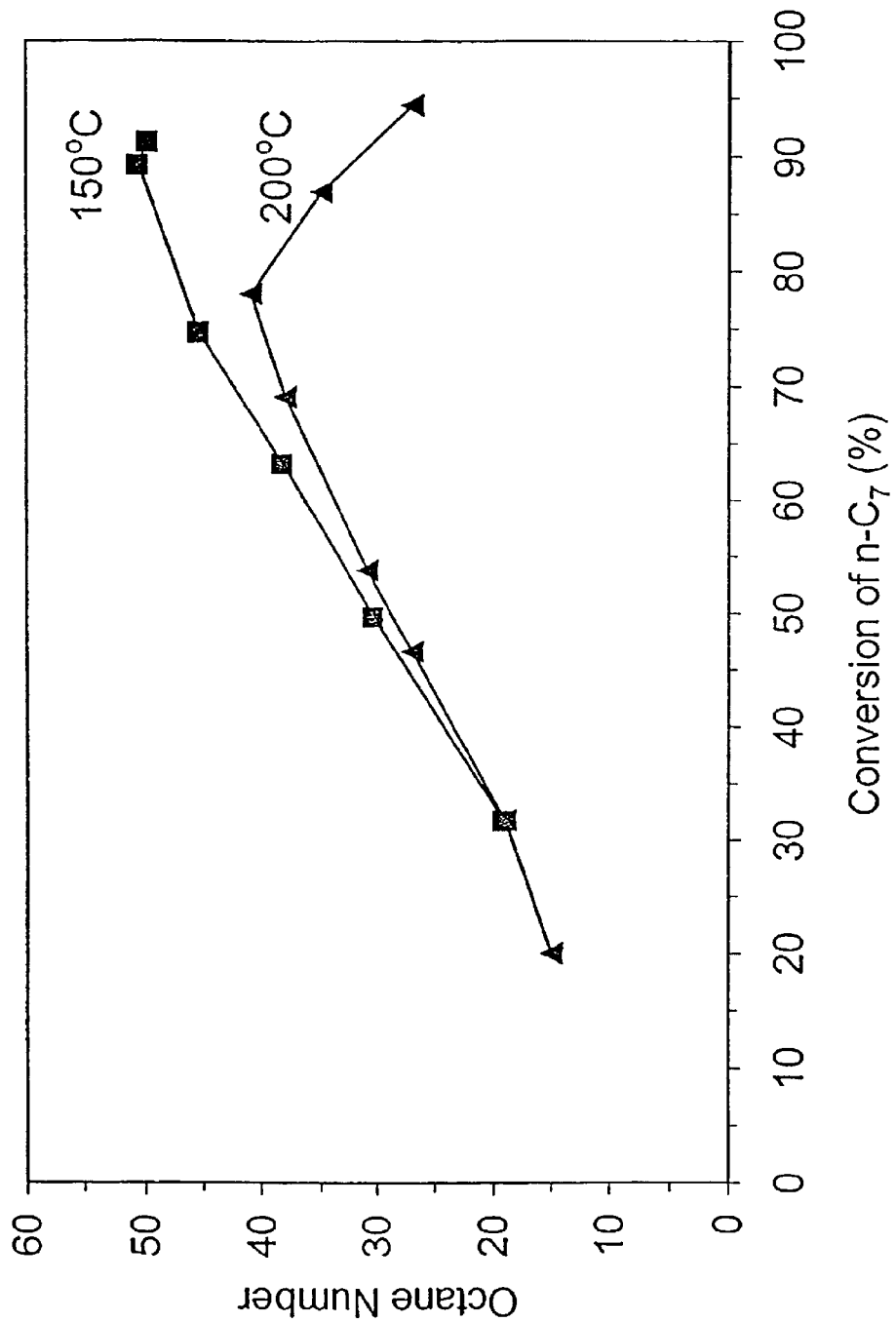
FIG. 5 depicts the octane number of n-heptane isomerization products and unconverted heptane over Pt/AlWZ (0.05, 800° C.) in $H_2$.

In an embodiment, the catalyst is used in an isomerization reaction with a greater than 50% conversion, and a greater than 60% selectivity. At 200° C., 85% isomerization selectivity was obtained at 63% conversion of n-heptane over Pt/AlWZ(0.05, 800° C.) (FIG. 3). Considering that the conversion rate of n-heptane over Pt/AlWZ(0.05, 800° C.) was very high at 200° C. (about 16 μmol n-C$_7$/s/g initially), the reaction temperature was lowered to 150° C. At 150° C., undoped Pt/WZ(800° C.) was not active, but Pt/AlWZ(0.05, 800° C.) was still active enough to convert n-C$_7$ at a rate of 1.1 μmol/s/g with a significantly improved isomerization selectivity. Isomerization selectivity was as high as 85% at 90% conversion of n-heptane (FIG. 4). Besides the overall isomerization selectivity, the percent of multi-branched isomers in the isomer products is of great interest since the octane numbers of multi-branched isomers are much higher than that of mono-branched isomers. As shown in FIG. 4, the percent of multi-branched isomers increased rapidly with the percent conversion of n-heptane. Correspondingly, the octane number increased from 0 to 50 and 40 through n-heptane isomerization at 150° C. and 200° C., respectively, over Pt/AlWZ(0.05, 800° C.) (FIG. 5).

Figure 6:
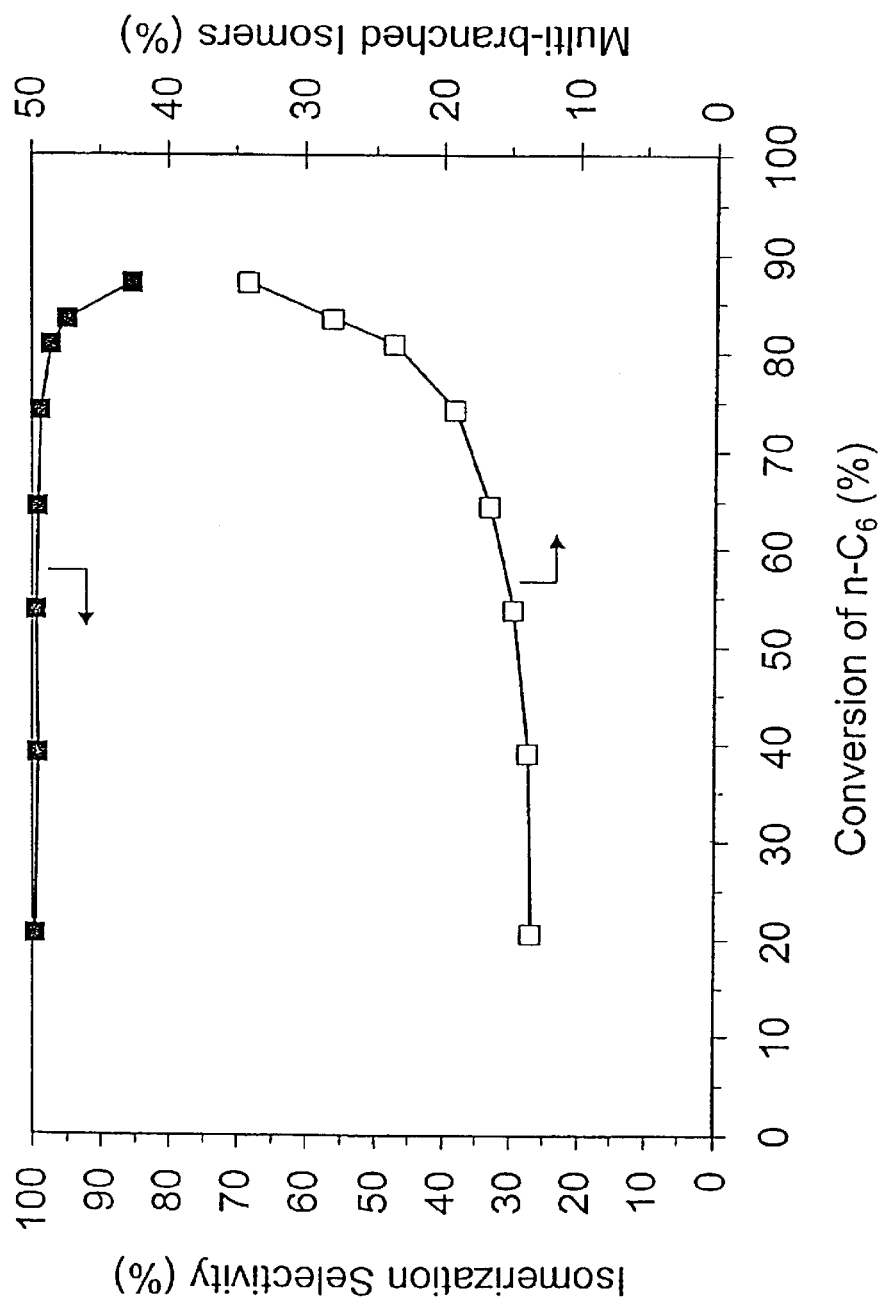
FIG. 6 depicts the n-hexane isomerization selectivity vs. conversion over Pt/AlWZ(0.05, 800° C.) at 200° C. in $H_2$.
Figure 7:
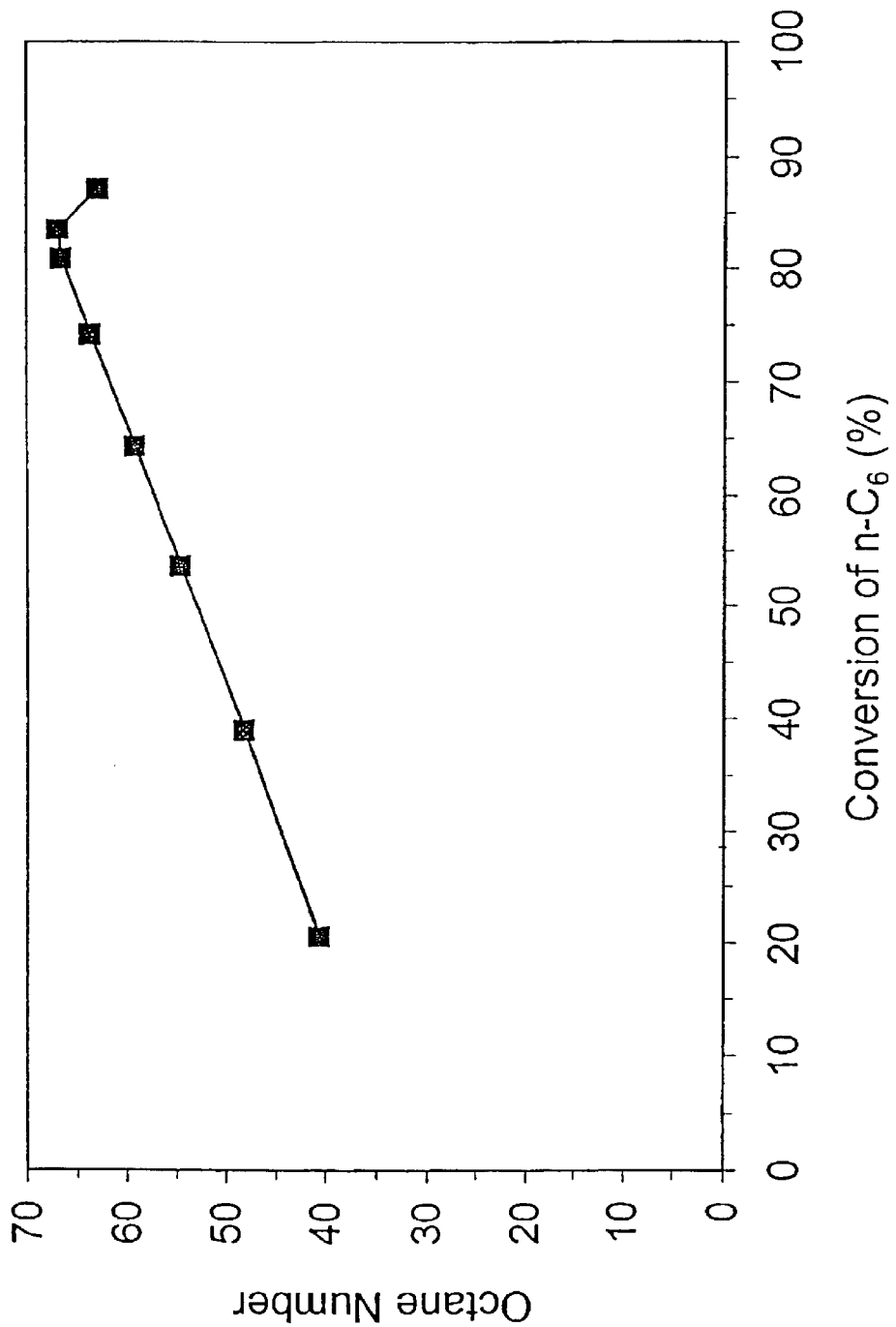
FIG. 7 depicts the octane number of n-hexane isomerization products and unconverted hexane over Pt/AlWZ(0.05, 800° C.) at 200° C. in $H_2$.

In an embodiment, the catalyst of the present invention is used in an alkane or alkyl moiety isomerization reaction to increase the octane number. In another embodiment, Pt/AlWZ(0.05, 800° C.) increases the octane number to greater than 50, greater than 60. For example, the Pt/AlWZ (0.05, 800° C.) could convert n-hexane at a high rate of 3.2 μmol/s/g at 200° C. At 85% conversion, >90% isomerization selectivity was maintained (FIG. 6). The percent of multi-branched isomers in the isomerization products could reach 35% at 85% isomerization selectivity. As a result, the octane number increased from 32 to 66 through n-hexane isomerization at 200° C. (FIG. 7).

Figure 8:
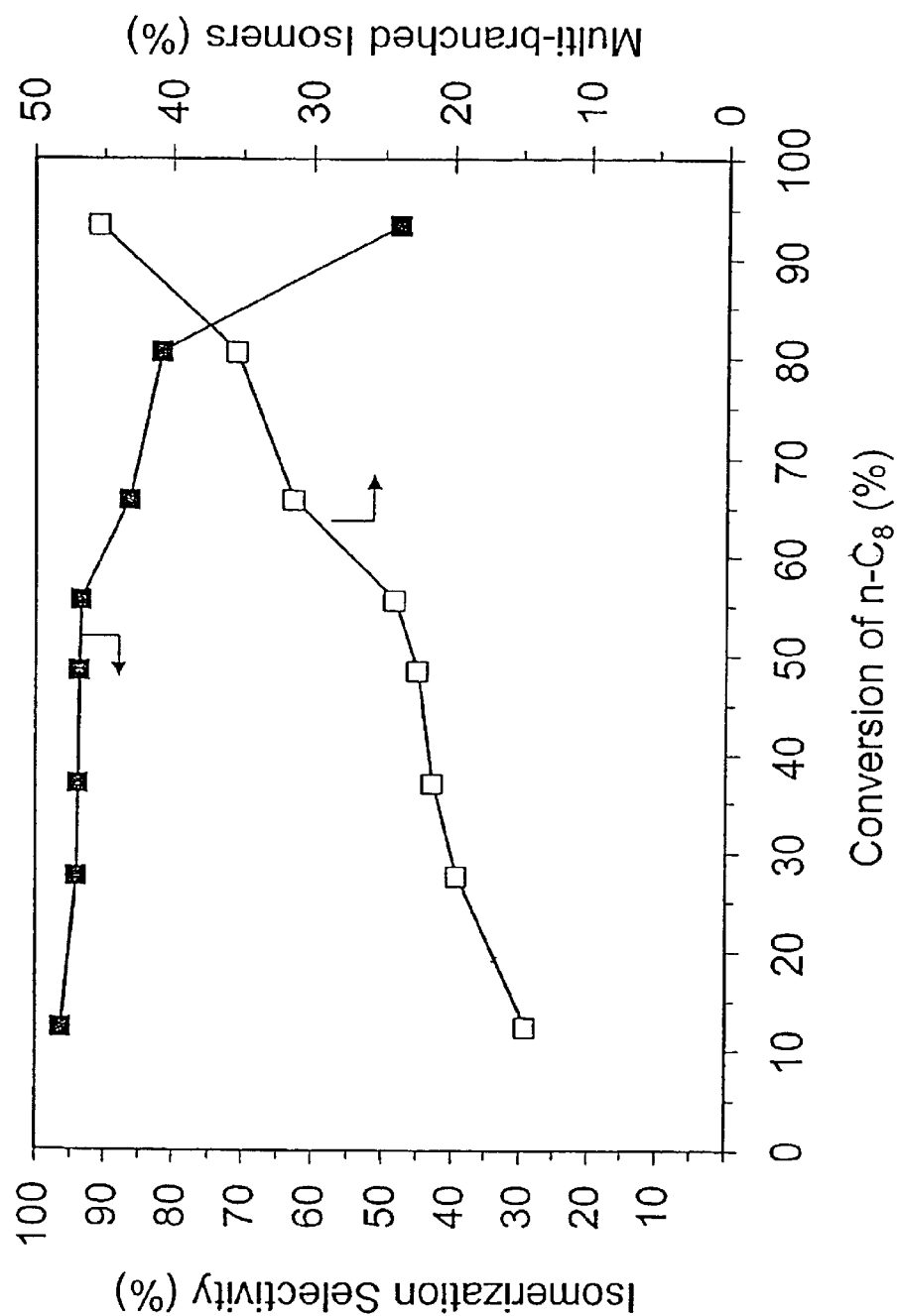
FIG. 8 depicts the n-octane isomerization selectivity vs. conversion over Pt/AlWZ(0.05, 800° C.) at 150° C. in $H_2$.

The isomerization of n-octane over Pt/AlWZ(0.05, 800° C.) may take place at 150° C. with a rate of 6.4 μmol/s/g. The isomerization selectivity was also excellent (FIG. 8). At 80% conversion, 81.% isomerization selectivity was obtained with 35% multi-branched isomers.

The chemical composition and physical properties of Pt/WO$_3$/ZrO$_2$ with different dopants are summarized in Table 1. Most dopants decreased the surface area of Pt/WO$_3$/ZrO$_2$, only Cr$^{3+}$, In$^{3+}$ and low Al$^{3+}$ doping level led to a slight increase in surface area. When activity values were converted from the unit of μmol/s/g to the unit of μmol/hr/m$^2$, the catalyst activity of Pt/MWZ(0.05, 800° C.) still differed significantly depending on the dopant introduced, and decreased in the order of Ga$^{3+}$≅Al$^{3+}$>Mg$^{2+}$>Co$^{2+}$>Fe$^{3+}$>Cr$^{3+}$>Y$^{3+}$>Si$^{4+}$>In$^{3+}$.

Figure 9:
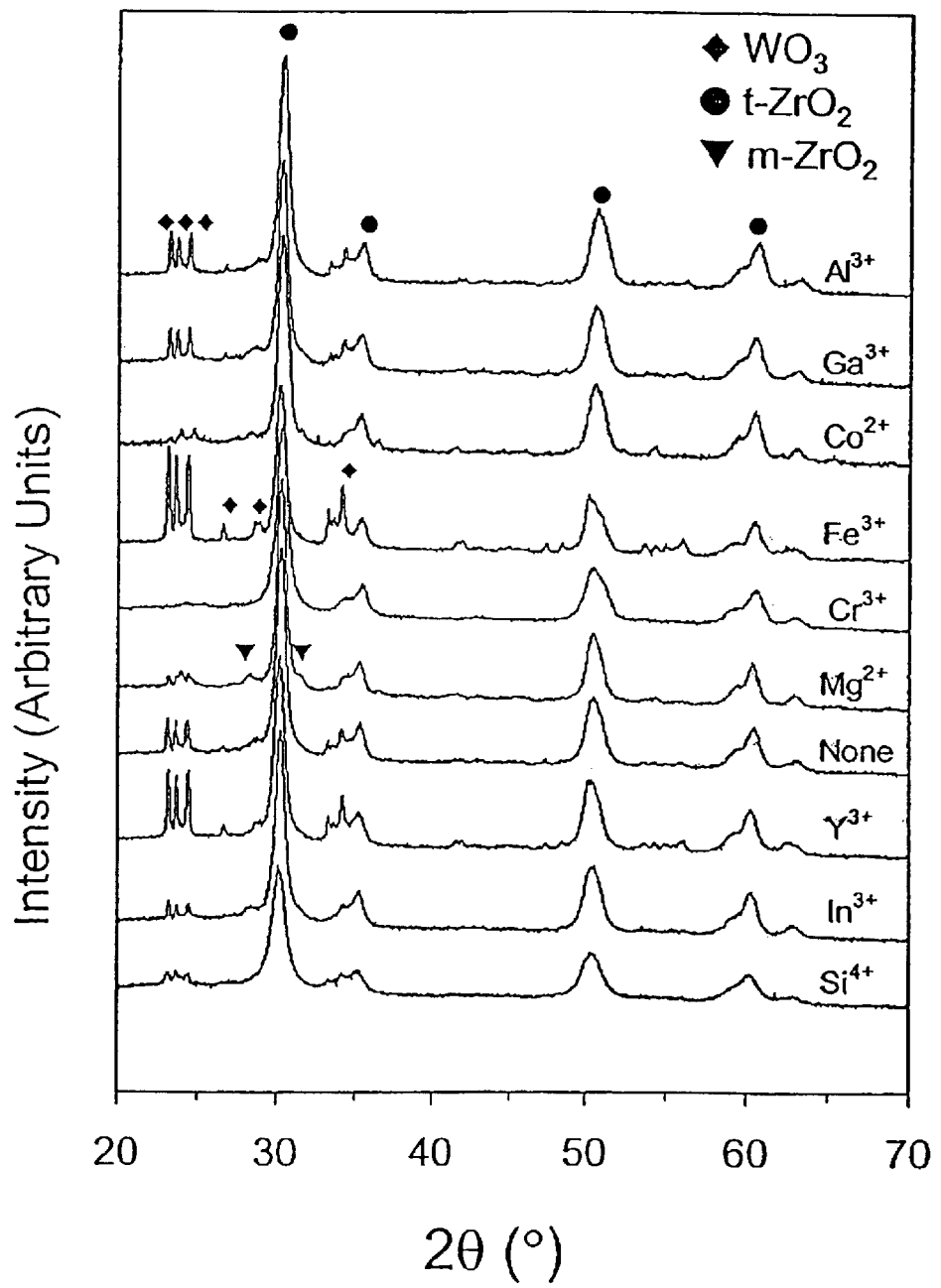
FIG. 9 depicts XRD patterns of $WO_3/ZrO_2$ with dopants (M/Zr=0.05, 800° C.).

The X-ray diffraction (XRD) patterns of tungstated zirconia with dopants are shown in FIG. 9. No diffraction peaks of dopant oxides were noted, indicating that the dopants were highly dispersed. The ZrO$_2$ was present mainly in tetragonal phase with crystallite sizes of 13–18 nm. The WO$_3$ diffraction peak intensities were quite different in these samples. Stronger WO$_3$ peaks were found in the XRD patterns of tungstated zirconia doped with Al$^{3+}$, Ga$^{3+}$, Fe$^{3+}$ and Y$^{3+}$.

Figure 10:
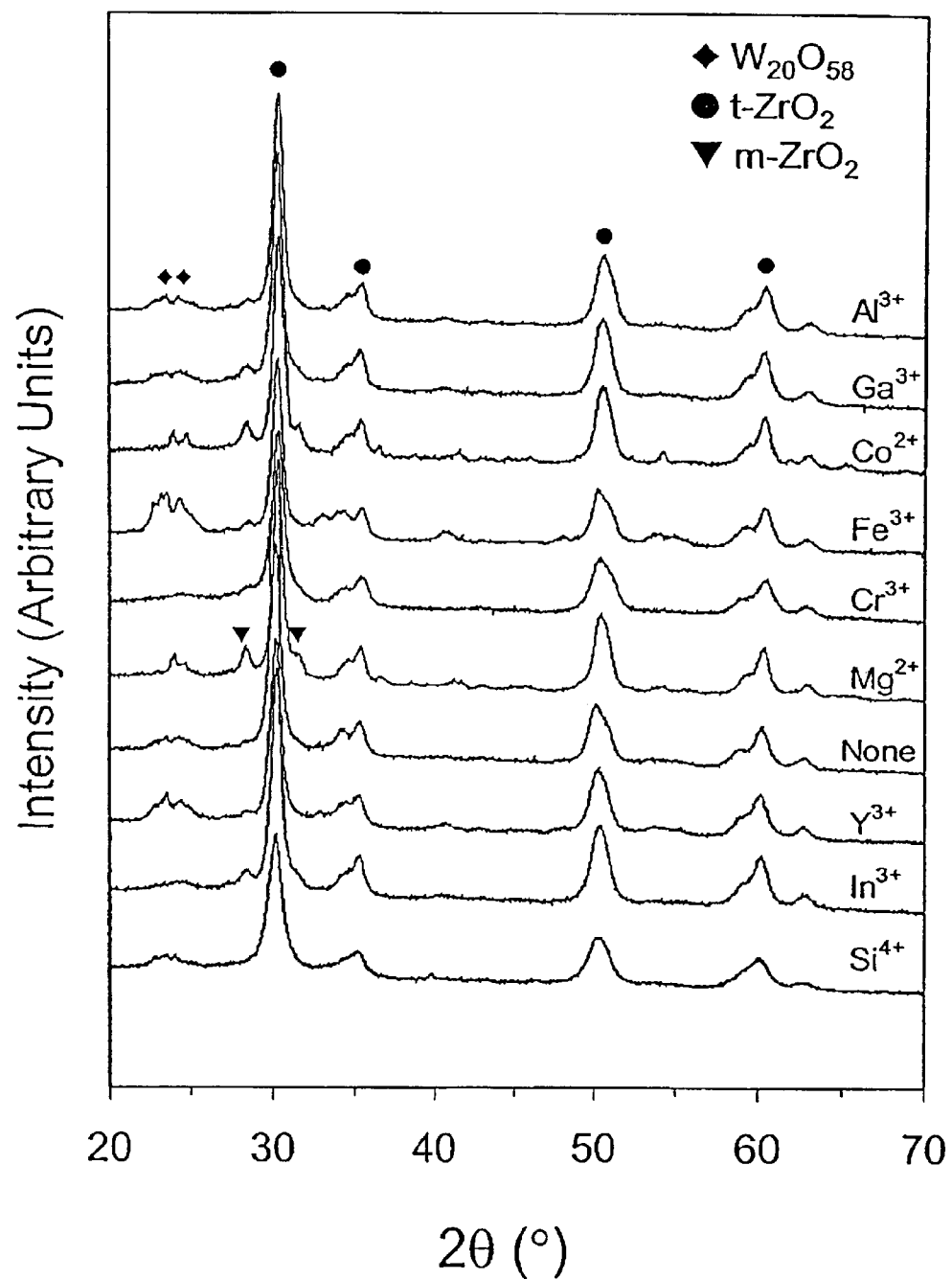
FIG. 10 depicts XRD patterns of $Pt/WO_3/ZrO_2$ with dopants (M/Zr=0.05, 800° C.) after reduction at 350° C. in $H_2$.

The Pt/MWZ catalysts were investigated by XRD after they were reduced at 350° C. in H$_2$ (FIG. 10). It was shown that WO$_3$ was reduced to W$_{20}$O$_{58}$ after the pretreatment in H$_2$. Zirconia was not affected in the process except for minor increase in monoclinic phase in some doped samples.

Figure 11:
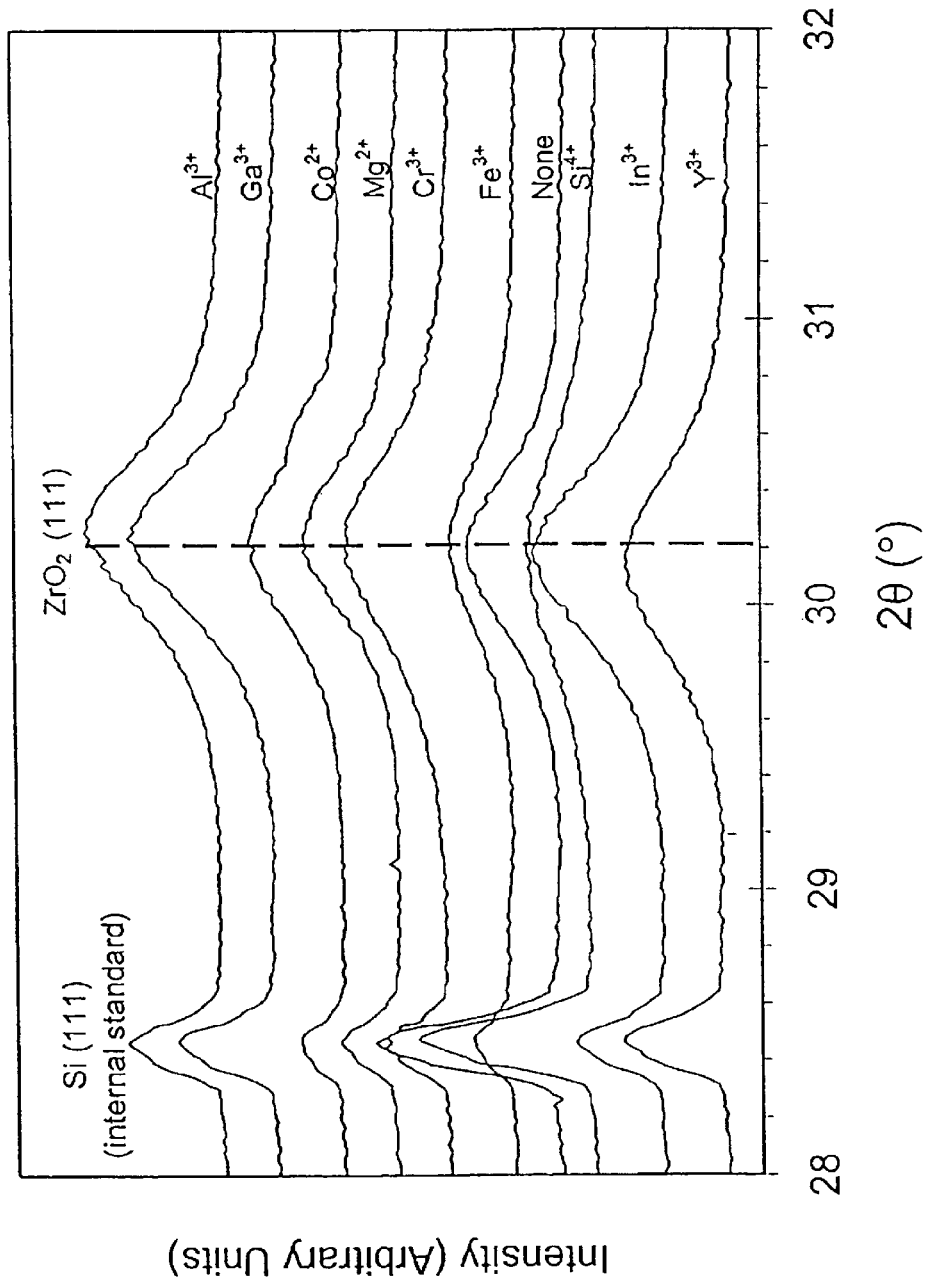
FIG. 11 depicts XRD patterns indicating $ZrO_2$ (111) peak shift in tungstated zirconia samples with different dopants (M/Zr=0.05, 800° C.).

Since there was no diffraction peak of dopant oxide in the XRD patterns of the various samples, the dopants must be highly dispersed. As most dopants are different in ionic radius from $Zr^{4+}$, the substitution of $Zr^{4+}$ by the dopant would lead to changes in the $ZrO_2$ unit cell. Using silicon as an internal reference in XRD studies, the position of zirconia (111) peak for various doped samples were examined (FIG. 11). For dopants with a smaller ionic radius than $Zr^{4+}$, the zirconia (111) peak did shift to higher angles except for SiWZ. Dopants with a larger ionic radius than $Zr^{4+}$ caused the shift of zirconia (111) peak to lower angles. These findings suggested that all dopants except $Si^{4+}$ could substitute for $Zr^{4+}$ in the crystal structure of zirconia. For the Pt/SiWZ catalyst, Si was likely present as a silica gel coating instead of a structural dopant for $ZrO_2$; this silica gel might have weakened the interaction between zirconia and tungsten oxide, resulting in the reduction in catalyst activity.

Figure 12:
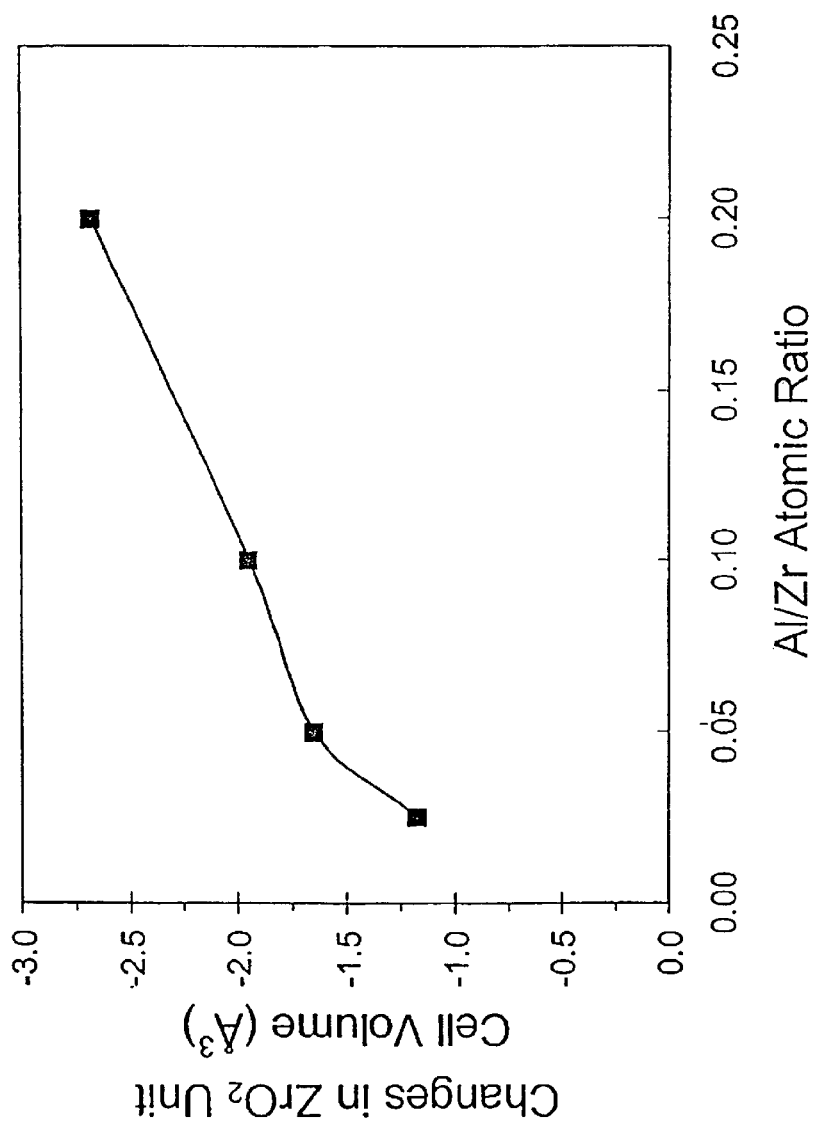
FIG. 12 depicts the change in $ZrO_2$ unit cell volume with the $Al^{3+}$ doping level in Pt/AlWZ(800° C.).

For Pt/AlWZ catalysts, the isomerization activity was maximized at a Al/Zr ratio of 0.05 (FIG. 2). FIG. 12 showed that the amount of zirconia unit cell volume reduction was smaller when the Al/Zr ratio was increased beyond 0.05, which implied that some of the $Al^{3+}$ dopants did not substitute for $Zr^{4+}$ at high $Al^{3+}$ loadings. Instead, they might have formed a surface $Al_2O_3$ coating, which compromised the promotional effect of $Al^{3+}$ dopants in alkane isomerization.

Figure 13:
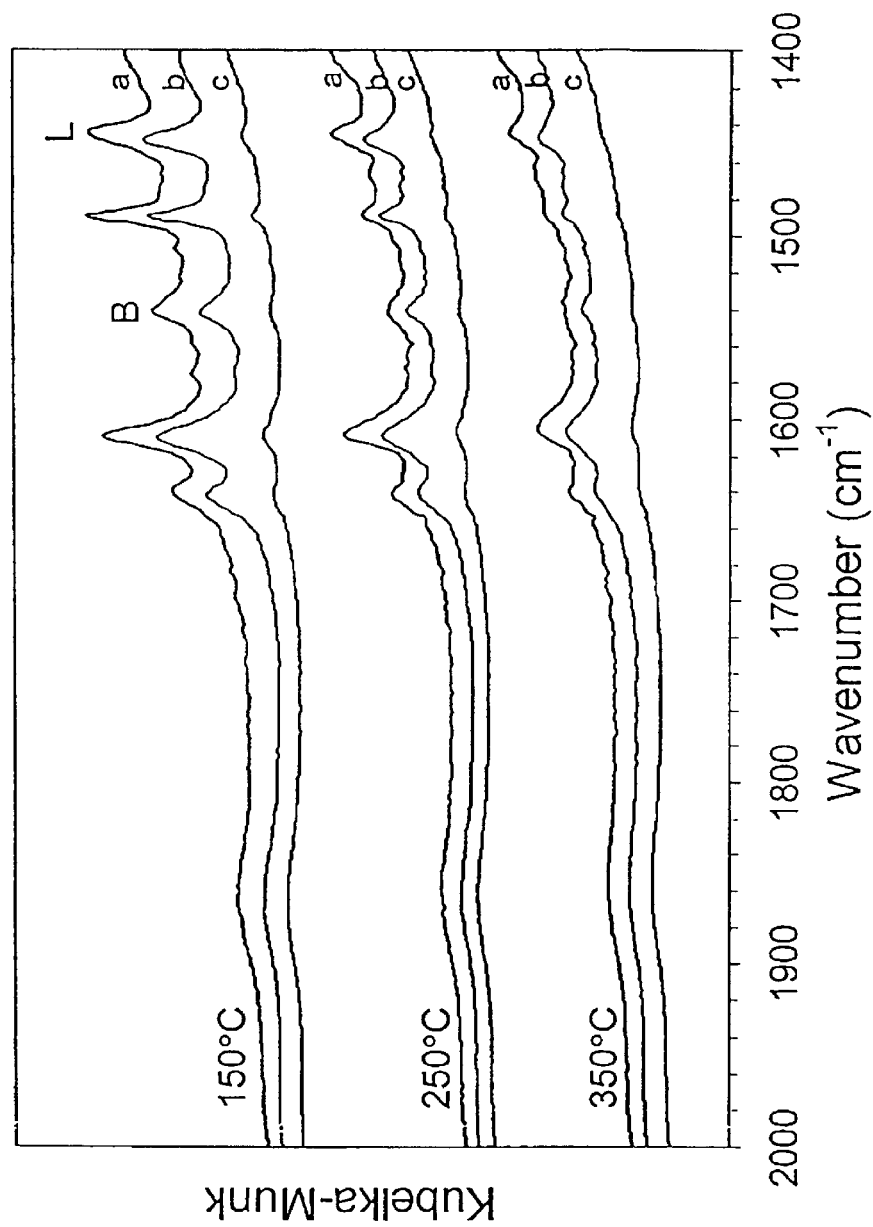
FIG. 13 depicts the DRIFT spectra of pyridine adsorbed over 350° C.—reduced (a) Pt/WZ(800° C.), (b) Pt/AlWZ (0.05, 800° C.) and (c) Pt/SiWZ(0.05, 800° C.), obtained after pyridine desorption at the specified temperatures.

The acidity of $Pt/WO_3/ZrO_2$ with and without dopants was characterized by pyridine-adsorption with DRIFT spectroscopy. The catalyst was pretreated in air and then reduced in $H_2$ for 1.5 hr. The reduced sample was mixed with 20 wt % silica gel as an internal reference. After grinding to a fine powder with particle size below 74 $\mu$m, the sample was loaded into the DRIFT cell. The sample was pretreated in dry He at 450° C. for 1 hr before pyridine was introduced at room temperature. After 30 min of pyridine adsorption, the sample was purged in flowing He at 150° C., 250° C. and 350° C. for 1 hr. DRIFT spectrum was taken near the end of purging at each desorption temperature. The DRIFT spectra of three representative samples, Pt/WZ(800° C.), Pt/AlWZ (0.05, 800° C.) and Pt/SiWZ(0.05, 800° C.), are shown in FIG. 13. The peak intensities of adsorbed pyridine on each sample were normalized to the Si—O—Si peak intensity at 1862 $cm^{-1}$. The peaks at 1540 $cm^{-1}$ and 1445 $cm^{-1}$ correspond to Brønsted and Lewis acid sites, respectively. At each desorption temperature, the least active Pt/SiWZ(0.05, 800° C.) had very weak peaks at 1540 $cm^{-1}$ and 1445 $cm^{-1}$ compared to Pt/WZ(800° C.) and Pt/AlWZ(0.05, 800° C.). The quantitative comparison of peak intensities at 1540 $cm^{-1}$ and 1445 $cm^{-1}$ for different doped samples are listed in Table 2. Most dopants, except $Si^{4+}$ and $Fe^{3+}$, did not change the acidity of $Pt/WO_3/ZrO_2$ by very-much. $Si^{4+}$ dopant reduced the amount of the acid sites dramatically and there were negligible strong acid sites in Pt/SiWZ(0.05, 800° C.). $Fe^{3+}$ dopant led to fewer and weaker Brønsted acid sites. For Pt/AlWZ, a higher doping level of Al/Zr=0.2 led to reduced Bronsted acidity. Strong acid sites were important and necessary for the isomerization reaction, but not the only factor in determining the activity of the catalyst.

Figure 14:
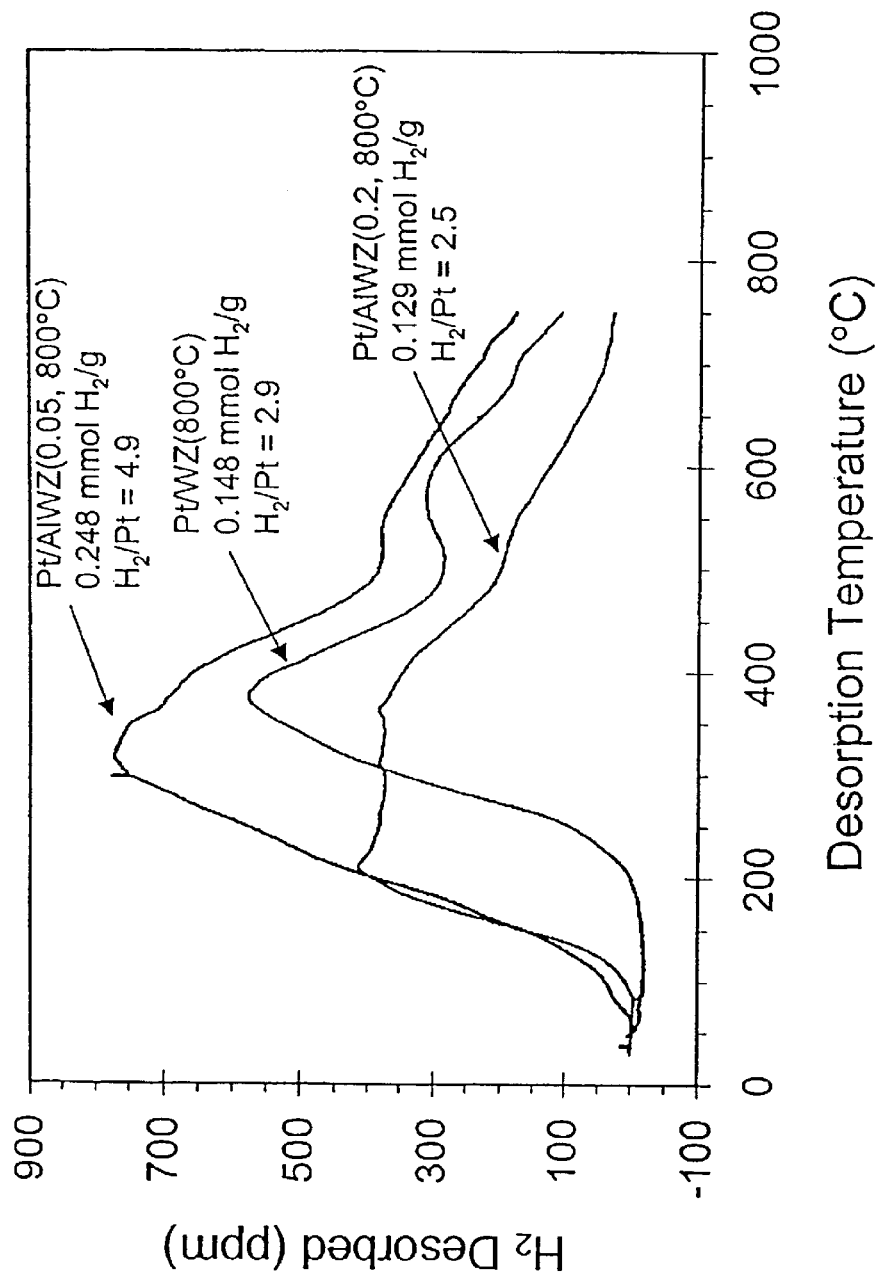
FIG. 14 depicts the temperature-programmed desorption of hydrogen over Pt/WZ(800° C), Pt/AlWZ(0.05, 800° C.) and Pt/AlWZ(0.2, 800° C.).

The amount of $H_2$ adsorbed over the catalysts was measured through temperature-programmed desorption of hydrogen ($H_2$-TPD) over doped and undoped catalysts. The catalysts were pretreated under the same condition as that prior to the reaction. After the adsorption of $H_2$ at 30° C. for 2 hr, the samples were exposed to flowing argon to remove weakly adsorbed hydrogen. Then $H_2$ desorption study was initiated by heating the catalyst bed at a rate of 5° C./min in flowing argon under atmospheric pressure, and the effluent gas was analyzed using a thermal conductivity detector. As shown in FIG. 14, $H_2$ desorption occurred about 150° C. lower on Pt/AlWZ compared to Pt/WZ, and the total amount of $H_2$ desorbed from Pt/AlWZ(0.05, 800° C.) was about 1.7 times of that from Pt/WZ(800° C.). This difference in $H_2$ desorption characteristics might account for the difference in catalyst activity between doped and undoped Pt/WZ sample. The abnormally high $H_2$/Pt molar ratio suggested a $H_2$ spillover effect. Since Pt dispersion over these samples was similar and no difference in Pt binding energy was observed from X-ray photoelectron spectroscopy (SSX-100 ESCA Spectrometer), the lower $H_2$ desorption temperature and greater $H_2$ desorption amount over Pt/AlWZ(0.05, 800° C.) could be attributed to structural changes from the inclusion of $Al^{3+}$.

Figure 15:
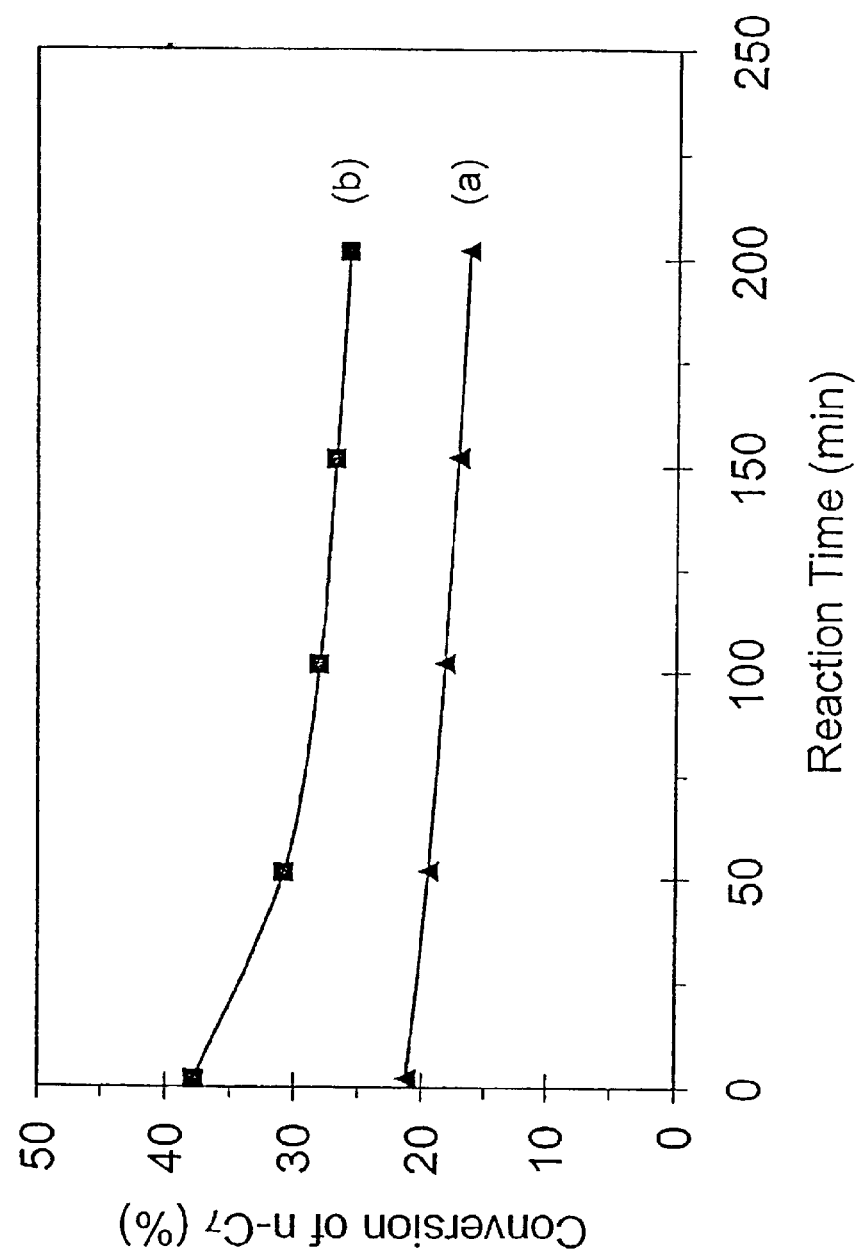
FIG. 15 depicts the n-heptane conversion vs. reaction time over (a) Pt/AlWZ(0.05, 800° C.) and (b) Pt/AlWZ(0.05, pH 10, 800° C.) (reaction condition: 38 mg catalyst, 200° C., ~6% n-$C_7$ in $H_2$, VHSV=110,000 $hr^{-1}$).

In one embodiment, the metallic dopant is introduced at controlled pH values. In another embodiment, the metallic dopant is introduced at pH 10. Because the initial precipitation pH values for $Zr^{4+}$ and various dopants were different, the precipitation of $Zr^{4+}$ and dopants may begin at different points in time. By controlling pH precipitation the catalyst nanostructure and composition may be optimized. To increase the homogeneity of the doped zirconia, $Zr^{4+}$ and dopant cations were precipitated under a constant pH of 10 (see Example 5). By using controlled pH precipitation, the catalyst obtained (Pt/AlWZ(0.05, pH 10, 800° C.)) gave rise to significantly higher activity compared to Pt/AlWZ(0.05, 800° C.) (see FIG. 15).

Figure 16:
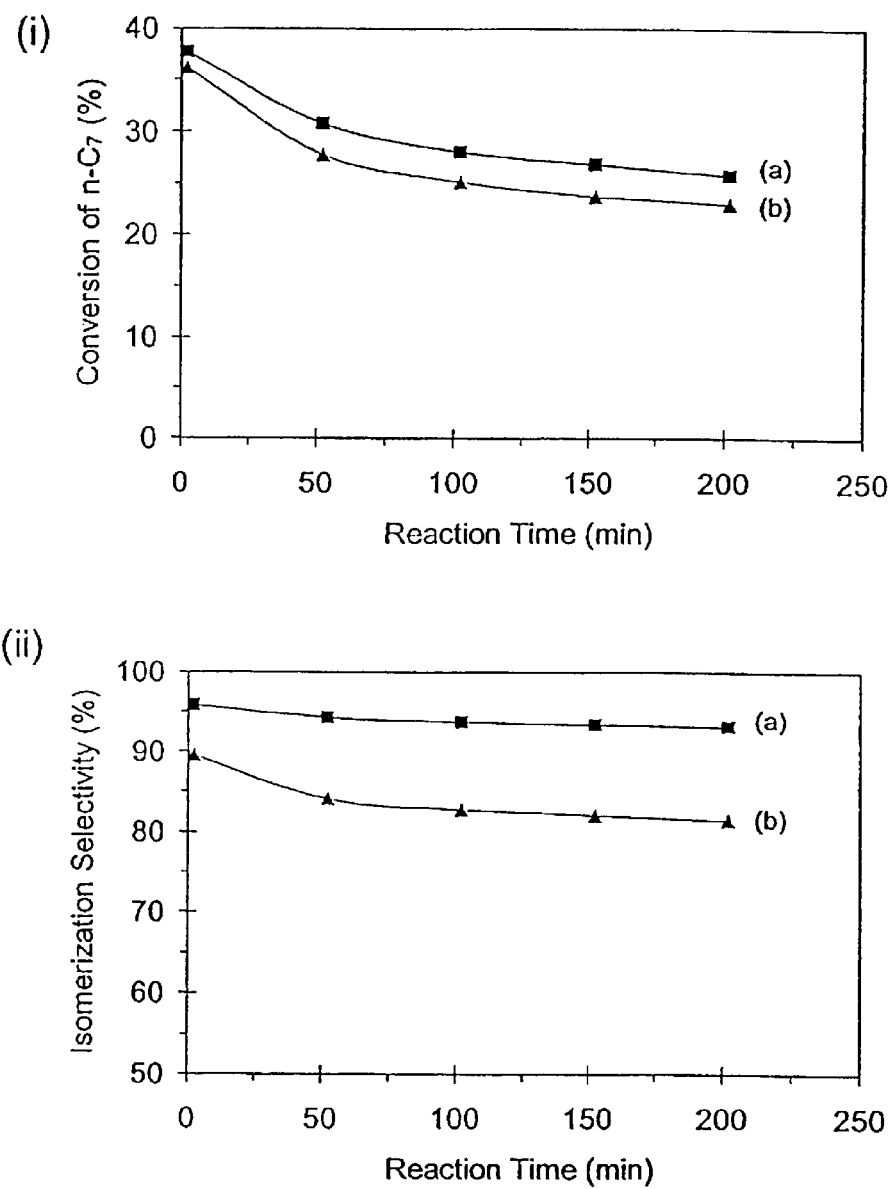
FIG. 16 depicts the (i) n-heptane conversion and (ii) isomerization selectivity vs. reaction time over Pt/AlWZ (0.05, pH 10, 800° C.) prepared with (a) $(NH_3)_4Pt(NO_3)_2$ and (b) $H_2PtCl_6$ (reaction condition: 38 mg catalyst, 200° C., ~6% n-$C_7$ in $H_2$, VHSV=110,000 hd $^{-1}$).
Figure 17:
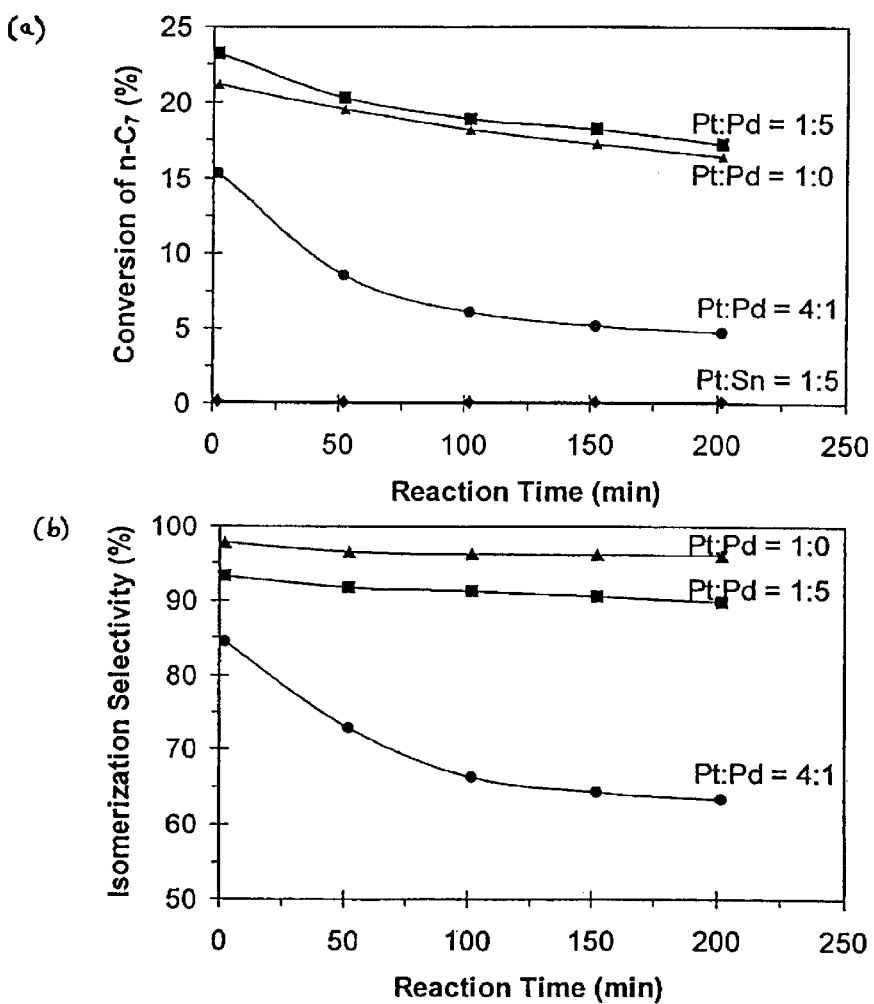
FIG. 17a depicts n-heptane conversion vs. reaction time over AlWZ(0.05, 800° C.) with (i) Pt, (ii) 4:1 Pt—Pd alloy, (iii) 1:5 Pt—Pd alloy and (iv) 1:5 Pt—Sn alloy (reaction condition: 38 mg catalyst, 200° C., ~6% n-$C_7$ in $H_2$, VHSV=110,000 $hr^{-1}$).
FIG. 17b depicts isomerization selectivity vs. reaction time over AlWZ(0.05, 800° C.) with (i) Pt, (ii) 4:1 Pt—Pd alloy and (iii) 1:5 Pt—Pd alloy (reaction condition: 3,8 mg catalyst, 200° C., ~6% n-$C_7$ in $H_2$, VHSV=110,000 $hr^{-1}$).

The precursor used for Pt also affected the activity and selectivity of the resulting Pt/AlWZ(0.05, pH 10, 800° C.) (FIG. 16). By using $(NH_3)_4Pt(NO_3)_2$ as the Pt precursor instead of $H_2PtCl_6$, a more active and selective Pt/AlWZ (0.05, pH 10, 800° C.) catalyst was obtained for the isomerization of n-heptane. In one embodiment, the noble metal may be varied to optimize isomerization of n-alkyls; however, it is also possible to use non-noble metals in the isomerization catalysts. Table 3 shows various noble metals in the compound of the present invention. In another embodiment, a noble metal alloy may be used (FIG. 17).

In an embodiment, the 1:5 Pt—Pd alloy could be used to give a slightly higher activity than Pt for AlWZ(0.05, 800° C.), but the latter provided for a higher isomerization selectivity. Other alloys such as Pt—Sn or Pt—Ge may be used to reduce the initial catalyst deactivation while retaining the high isomerization selectivity of the AlWZ system.

Figure 18:
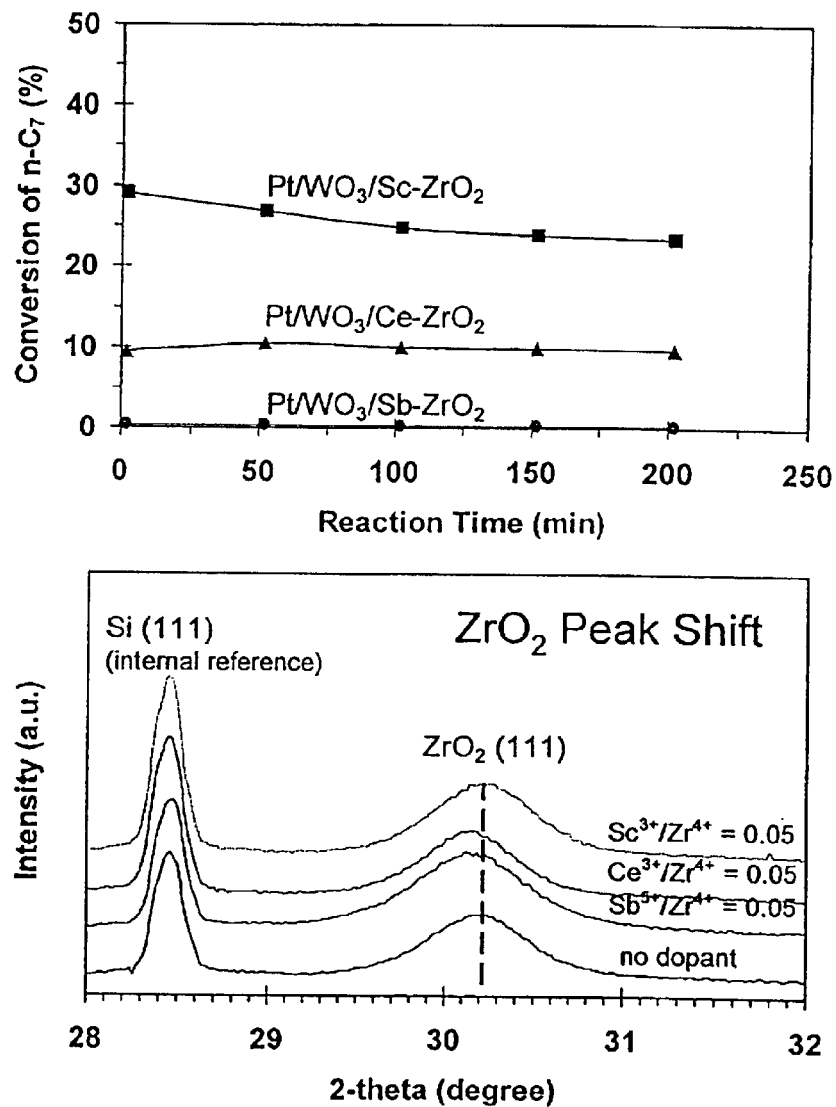
FIG. 18 depicts the effect of dopant oxides having similar crystal structure as $ZrO_2$.
Figure 19:
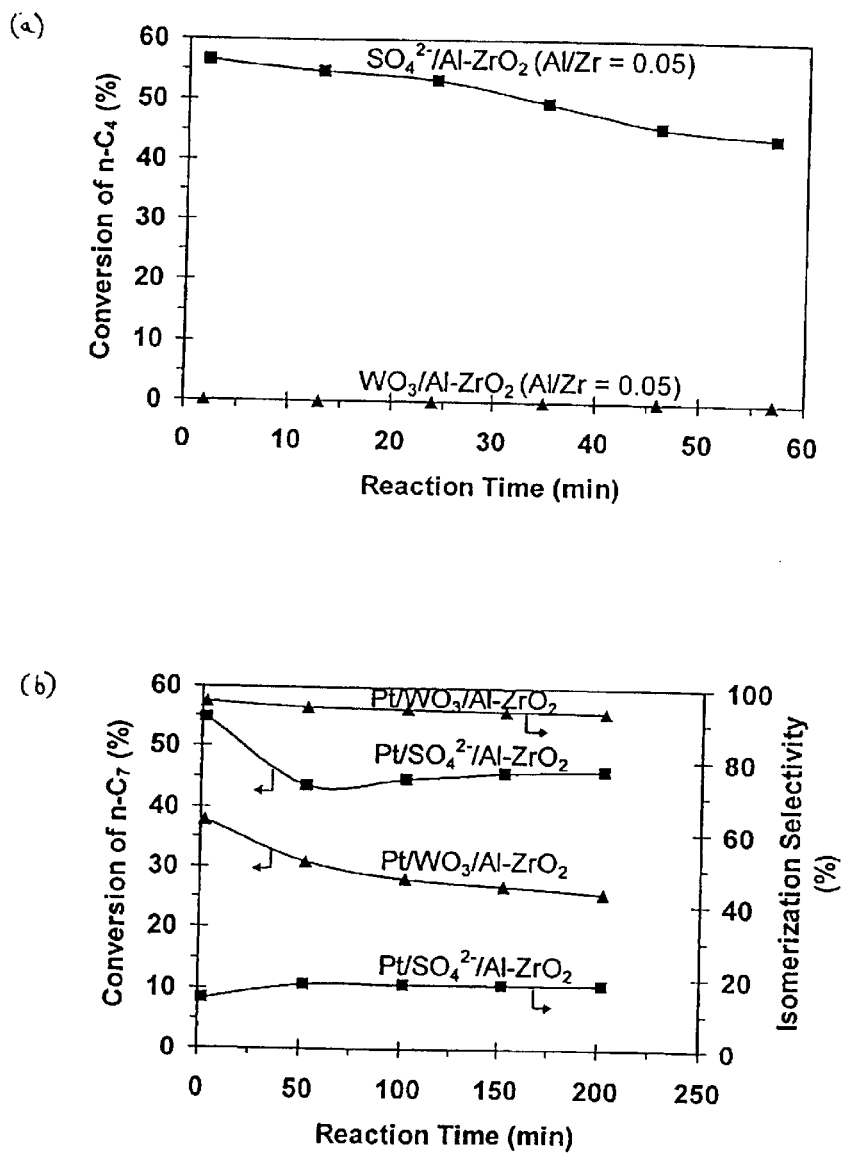
FIG. 19a depicts n-butane conversion over reaction time and the effect of different anions on the activity of Pt/anion/Al—$ZrO_2$ (reaction condition: 250 mg catalyst, 250° C., ~2.47% n-$C_4$ in $H_2$, VHSV=8,000 $hr^{-1}$).
FIG. 19b depicts n-heptane conversion over reaction time and the effect of different anions on the activity and selectivity of Pt/anion/Al—$ZrO_2$ (reaction condition: 38 mg catalyst, 200° C., ~6% n-$C_7$ in $H_2$, VHSV=110,000 $hr^{-1}$).

In one embodiment, the dopant metals may be varied to optimize catalytic behavior. FIG. 18 shows the isomerization of n-alkanes using various dopant oxides with 38 mg of catalyst reduced at 350° C. in $H_2$ for 1.5 hours. The reaction was run at 200° C. In an embodiment, the metallic oxide anion may be varied to optimize isomerization selectivity. In another embodiment, the metallic oxide anion is $SO_4^{2-}$ or $WO_3$ (FIG. 19).

Nanocomposite Pt/tungstated zirconia catalysts with dopants such as $Al^{3+}$ and $Ga^{3+}$ were much more active and selective than conventional Pt/tungstated zirconia in the isomerization of hexane, heptane and octane. Nanocomposite processing provides for an ultrahigh dispersion of components, allowing for the effective substitution of dopant cations within the zirconia lattice. The resulting Pt/tungstated doped zirconia allows for low-temperature conversion of mid-distillates, greater $H_2$ adsorption, and a low $H_2$ desorption temperature. Such system may also be used for the effective isomerization of other hydrocarbons with negligible catalyst deactivation over time.

TABLE 1

Chemical Composition and Physical Properties of Various Doped $Pt/WO_3/ZrO_2$.

| Sample | Chemical Composition* | | | S. A. | Activity at 2 hr TOS | |
|---|---|---|---|---|---|---|
| | Dopant/Zr | W (wt %) | Pt (wt %) | ($m^2/g$) | ($\mu mol/s/g$) | ($\mu mol/hr/m^2$) |
| Pt/WZ(800° C.) | 0 | 16 | 1.0 | 63 | 5.0 | 286 |
| Pt/AlWZ(0.05, 800° C.) | 0.05 | 16 | 1.0 | 56 | 12.9 | 829 |
| Pt/GaWZ(0.05, 800° C.) | 0.05 | 16 | 1.0 | 57 | 13.2 | 834 |
| Pt/CoWZ(0.05, 800° C.) | 0.05 | 16 | 1.0 | 60 | 8.9 | 534 |
| Pt/MgWZ(0.05, 800° C.) | 0.05 | 16 | 1.0 | 53 | 9.0 | 611 |
| Pt/FeWZ(0.05, 800° C.) | 0.05 | 16 | 1.0 | 49 | 5.4 | 397 |
| Pt/CrWZ(0.05, 800° C.) | 0.05 | 16 | 1.0 | 77 | 7.5 | 351 |
| Pt/YWZ(0.05, 800° C.) | 0.05 | 16 | 1.0 | 48 | 3.5 | 263 |
| Pt/InWZ(0.05, 800° C.) | 0.05 | 16 | 1.0 | 68 | 0.17 | 9 |
| Pt/SiWZ(0.05, 800° C.) | 0.05 | 16 | 1.0 | 22 | 0.12 | 20 |
| Pt/AlWZ(0.025, 800° C.) | 0.025 | 16 | 1.0 | 65 | 9.9 | 548 |
| Pt/AlWZ(0.1, 800° C.) | 0.1 | 16 | 1.0 | 44 | 9.2 | 753 |
| Pt/AlWZ(0.2, 800° C.) | 0.2 | 16 | 1.0 | 37 | 4.3 | 418 |

*Nominal composition from synthesis conditions.

TABLE 2

The Amount of Brønsted and Lewis Acid Sites in Reduced $Pt/WO_3/ZrO_2$ With and Without Dopants.

| Sample | Desorption Temperature (° C.) | Brønsted Acid Sites* | Lewis Acid Sites* |
|---|---|---|---|
| Pt/WZ(800° C.) | 150 | 0.46 | 0.93 |
| | 250 | 0.28 | 0.43 |
| | 350 | 0.14 | 0.25 |
| Pt/AlWZ(0.05, 800° C.) | 150 | 0.54 | 0.51 |
| | 250 | 0.26 | 0.46 |
| | 350 | 0.12 | 0.32 |
| Pt/SiWZ(0.05, 800° C.) | 150 | 0.096 | 0.098 |
| | 250 | 0.050 | 0.031 |
| | 350 | 0.029 | 0.023 |
| Pt/GaWZ(0.05, 800° C.) | 250 | 0.29 | 0.33 |
| | 350 | 0.18 | 0.25 |
| Pt/CoWZ(0.05, 800° C.) | 250 | 0.35 | 0.50 |
| | 350 | 0.17 | 0.35 |
| Pt/MgWZ(0.05, 800° C.) | 250 | 0.36 | 0.46 |
| | 350 | 0.18 | 0.34 |
| Pt/CrWZ(0.05, 800° C.) | 250 | 0.34 | 0.90 |
| | 350 | 0.15 | 0.63 |
| Pt/FeWZ(0.05, 800° C.) | 250 | 0.17 | 0.31 |
| | 350 | 0.067 | 0.27 |
| Pt/YWZ(0.05, 800° C.) | 250 | 0.25 | 0.42 |
| | 350 | 0.11 | 0.21 |
| Pt/InWZ(0.05, 800° C.) | 250 | 0.35 | 0.51 |
| | 350 | 0.15 | 0.33 |
| Pt/AlWZ(0.2, 800° C.) | 150 | 0.28 | 0.72 |
| | 250 | 0.16 | 0.50 |
| | 350 | 0.077 | 0.32 |

*The amounts of Brønsted and Lewis acid sites were determined by the ratio of peak intensity at 1540 $cm^{-1}$ and 1445 $cm^{-1}$, respectively, over the peak intensity at 1862 $cm^{-1}$.

TABLE 3

Influence of Different Noble Metals.

| Metal | Loading (wt %) | Activity ($\mu mol/s/g$) | Conversion (%) | Isomerization (%) | Multi-branched Isomers (%) |
|---|---|---|---|---|---|
| Ru | 1.0 | 0.51 | 4.9 | 87.4 | 34.6 |
| Pd | 1.0 | 1.1 | 8.3 | 99.8 | 15.8 |
| Pt | 1.0 | 1.1 | 10.9 | 99.8 | 15.3 |
| | 0.1 | 0.15 | 5.8 | 91.4 | 34.5 |
| | 10.0 | 0.14 | 5.6 | 96.3 | 16.3 |

Exemplification

The invention now being generally described, it will be more readily understood by reference to the following examples, which are included merely for purposes of illustration of certain aspects and embodiments of the present invention, and are not intended to limit the invention.

EXAMPLE 1

0.161 mol of $ZrOCl_2.8H_2O$ (Aldrich) was mixed with 0.082 mol of $AlCl_3.6H_2O$ (Aldrich) in a 600 ml glass beaker. 320 ml of $H_2O$ were added to dissolve the salts with stirring. Then 14–28 wt % $NH_4OH$ was added dropwise to the solution under vigorous stirring until the final pH of the precipitation mixture reached 9.0. After stirring for more than 1 hr, the precipitate was washed by distilled water and recovered through centrifugation. Materials were usually washed 5–6 times to remove the chloride ions.

The precipitate was dried in oven at 120° C. overnight. Then, a calculated amount of ammonium metatungstate (99.9%, Strem) was added to the mixed hydroxide via the incipient wetness technique. After calcination at 600–950° C. for 3 hr, the tungstated $Al^{3+}$-doped zirconia obtained was impregnated with 1 wt % of Pt using the precursor $(NH_3)_4Pt(NO_3)_2$. After calcination at 450° C. for 3 hr, the final product was denoted as Pt/AlWZ(x, y) (x=nominal atomic ratio of Al/Zr, y=calcination temperature for tungstated Al-doped zirconia). Pt-loaded tungstated zirconia materials not doped with $Al^{3+}$ were denoted as Pt/WZ(y).

EXAMPLE 2

Different metal ions besides $Al^{3+}$ were co-precipitated with $Zr^{4+}$ at a dopant/Zr atomic ratio of 0.05, following the procedures described in Example 1. The chloride or nitrate salts of metal ions, such as $Ga^{3+}$, $Mg^{2+}$, $Co^{2+}$, $Cr^{3+}$, $Fe^{3+}$, $Y^{3+}$, and $In^{3+}$, were mixed with zirconyl chloride. The final pH of the precipitation mixture for all materials was 9.0, except for the $Mg^{2+}$-doped material, which was 10.0 to ensure complete $Mg^{2+}$ precipitation. The final materials loaded with tungstate and Pt were denoted Pt/MWZ(0.05, y), where M=dopant ion, y=calcination temperature for tungstate metal-doped zirconia.

EXAMPLE 3

Si(IV) was co-precipitated with zirconyl chloride using an alkoxide precursor, $Si(OC_2H_5)_4$, at the final pH of 9.0. The final $Si^{4+}$-doped catalyst loaded with tungstate and Pt was denoted as Pt/SiWZ(x, y).

EXAMPLE 4

Example 1 was repeated with different amounts of $AlCl_3.6H_2O$ and $ZrOCl_2.8H_2O$. Al/Zr ratios in the range of 0.025 to 0.20 were obtained.

EXAMPLE 5

The same protocol as Example 1 was used, but the precipitation of $Zr^{4+}$ and $Al^{3+}$ was conducted under the controlled pH condition. The pH was maintained at 10±0.2 by controlling the relative addition rate of the mixed salt solution to the addition rate of $NH_4OH$. The rest of the procedures was the same as that in Example 1. The final product was denoted as Pt/AlWZ(x, pH 10, y).

EXAMPLE 6

Besides $(NH_3)_4Pt(NO_3)_2$, other Pt precursor such as $H_2PtCl_6$ was used in the loading of 1 wt % Pt over tungstated doped zirconia. In addition to pure Pt, Pt alloys and other noble metals were also loaded over the tungstated doped zirconia.

EXAMPLE 7

Structural Characterization

The microstructure and surface properties of the nano-structured solid acid materials were analyzed using a variety of experimental techniques. Powder X-ray diffraction (XRD) data were recorded on a Siemens D5000 diffractometer operated at 45 kV and 40 mA, using nickel-filtered CuKα radiation with a wavelength of 1.5406 Å. Crystallite size was obtained by peak-broadening analysis using Scherrer's method. Nitrogen adsorption isotherms were obtained at 77 K on a Micromeritics ASAP 2010 Gas Sorption and Porosimetry System. Samples were degassed at 150° C. under vacuum until a final pressure of $1\times10^{-3}$ Torr was reached. BET (Brunauer-Emmett-Teller) surface areas were determined over a relative pressure range of 0.05 to 0.20.

EXAMPLE 8

Catalyst Acidity

The acidity of tungstated doped zirconia catalyst was analyzed by pyridine-adsorption infrared (IR) spectroscopy. The sample was reduced at 350° C. in $H_2$ for 1.5 hr before loading into a diffuse reflectance infrared Fourier-transform (DRIFT) cell. Amorphous silica was physically mixed with the sample as an internal standard (20 wt % $SiO_2$ total). The sample was pretreated in He at 450° C. for 1 hr before adsorption of pyridine at room temperature. IR spectra of the sample were recorded after desorption of pyridine in flowing He (45 ml/min) for 1 hr at 150° C., 250° C. and 350° C. on a Bio-Rad FTS-60A infrared spectrometer. The peak area of Si—O—Si at 1862 $cm^{-1}$ was used as the reference. The amounts of Brønsted acid and Lewis acid in the sample were linearly related to the peak areas at 1540 $cm^{-1}$ and 1445 $cm^{-1}$ respectively, so these peak areas could be used in the comparison of the amount of acidic sites in different samples.

EXAMPLE 9

Catalytic Activity

The isomerization of n-heptane was carried out in a downflow fixed-bed reactor under ambient pressure. The reaction took place at 150° C. or 200° C. The catalyst was secured in place with pretreated quartz wool just above a thermocouple. n-Heptane was brought into the reactor by $H_2$ flowing through n-heptane saturator at 25° C., with a $H_2$/n-heptane molar flow ratio of 16. The flow rate of $H_2$ or the amount of catalyst loaded was adjusted to get the desired conversion of n-heptane. For comparing different catalyst activity, n-heptane conversion was limited to about 20% to eliminate the effect of intraparticle mass transfer. The catalyst was pretreated in flowing air at 450° C. for 1.5 hr before contacting with the feed gas. The reaction products were analyzed by a HP 6890 gas chromatograph equipped with a flame ionization detector (FID) and with a 50-m HP-PLOT/ $Al_2O_3$ "KCl" deactivated capillary column. Isomerization reactions of n-hexane and n-octane were performed under the same conditions as above except under different partial pressures. The n-hexane saturator was immersed in an ice trap to obtain a $H_2$/n-hexane molar flow ratio of 16, and the n-octane saturator was set at 25° C. to obtain a $H_2$/n-octane molar flow ratio of 53.

Incorporation by Reference

All publications and patents mentioned herein are hereby incorporated by reference in their entirety, as if each individual publication or patent was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A catalytic compound represented by the formula:

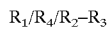

wherein:

$R_1$ is a metal, metal alloy, or bimetallic system;

$R_2$ is any metal dopant;

$R_3$ is a metallic oxide or mixtures of any metallic oxide;
$R_4$ is $WO_x$, $MoO_x$, $SO_4^{2-}$ or $PO_4^{3-}$; and
x is a whole or fractional number between 2 and 3 inclusive.

2. The catalytic compound of claim 1, wherein $R_1$ is a Group VIII metal.

3. The catalytic compound of claim 1, wherein $R_1$ is a combination of Group VIII metals.

4. The catalytic compound of claim 2, wherein $R_1$ is selected from the group consisting of platinum, palladium, iridium, rhodium, and combinations thereof.

5. The catalytic compound of claim 1, wherein $R_1$ is selected from the group consisting of an alloy and bimetallic systems Pt—Sn, Pt—Pd, and Pt—Ge.

6. The catalytic compound of claim 1, wherein $R_2$ is selected from the group consisting of $Al^{3+}$, $Ga^{3+}$, $Ce^{4+}$, $Sb^{5+}$, $Sc^{3+}$, $Mg^{2+}$, $Co^{2+}$, $Fe^{3+}$, $Cr^{3+}$, $Y^{3+}$, $Si^{4+}$, and $In^{3+}$.

7. The catalytic compound of claim 6, wherein $R_2$ is $Al^{3+}$.

8. The catalytic compound of claim 1, wherein $R_3$ is selected from the group consisting of zirconium oxide, titanium oxide, tin oxide, ferric oxide, and cerium oxide.

9. The catalytic compound of claim 8, wherein $R_3$ is $ZrO_2$.

10. The catalytic compound of claim 1, wherein the ratio of metal dopant to metal in the oxide is less than or equal to about 0.20.

11. The catalytic compound of claim 10, wherein the ratio of metal dopant to metal in the oxide is less than or equal to about 0.05.

12. The catalytic compound of claim 10, wherein the ratio of metal dopant to metal in the oxide is about 0.05.

13. The catalytic compound of claim 1, wherein $R_4$ is $WO_x$, wherein x is a whole or fractional number between 2 and 3 inclusive.

14. The catalytic compound of claim 13, wherein x is about 3.

15. The catalytic compound of claim 13, wherein x is about 2.9.

16. A method of alkane or alkyl moiety isomerization comprising the reaction step of contacting a catalyst with an alkyl, wherein said catalyst is represented by the formula:

wherein:

$R_1$ is a metal, metal alloy, or bimetallic system;
$R_2$ is any metal dopant;
$R_3$ is a metallic oxide or mixtures of any metallic oxide;
$R_4$ is $WO_x$, $MoO_x$, $SO_4^{2-}$ or $PO_4^{3-}$; and
x is a whole or fractional number between 2 and 3 inclusive.

17. The method of claim 16, wherein the alkane isomerization is a straight chain alkane isomerization.

18. The method of claim 17, wherein the alkane isomerization is a $C_4$–$C_{10}$ alkane isomerization.

19. The method of claim 18, wherein the alkyl isomerization is a $C_6$–$C_8$ alkane isomerization.

20. The method of claim 16, wherein the reaction step occurs at less than 210° C.

21. The method of claim 16, wherein the reaction step occurs at less than 170° C.

22. The method of claim 16, wherein the reaction step occurs at less than 150° C.

23. The method of claim 16, wherein the reaction yield is greater than 70%.

24. The method of claim 23, wherein the reaction yield is greater than 80%.

25. The method of claim 16, wherein the alkane isomerization increases the octane number of the alkane.

26. A compound represented by the formula $Pt/WO_3/Al$—$ZrO_2$.

* * * * *